United States Patent
Zhang et al.

(10) Patent No.: US 11,781,159 B2
(45) Date of Patent: Oct. 10, 2023

(54) FORMATION AND ISOLATION OF HYDROXYCARBOXYLIC ACIDS VIA A SOPHOROLIPID INTERMEDIATE

(71) Applicant: ExxonMobil Technology and Engineering Company, Annandale, NJ (US)

(72) Inventors: Xiaozhou Zhang, Bridgewater, NJ (US); Zarath M Summers, High Bridge, NJ (US); Partha Nandi, Annandale, NJ (US); Mark P Hagemeister, Morris Plains, NJ (US); Jihad M Dakka, Whitehouse Station, NJ (US); Mohor Chatterjee, Annandale, NJ (US); Vera Grankina, Union Dale, PA (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 428 days.

(21) Appl. No.: 17/068,147

(22) Filed: Oct. 12, 2020

(65) Prior Publication Data
US 2021/0108235 A1    Apr. 15, 2021

Related U.S. Application Data

(60) Provisional application No. 62/915,185, filed on Oct. 15, 2019.

(51) Int. Cl.
| | |
|---|---|
| C12P 7/42 | (2006.01) |
| C07C 51/377 | (2006.01) |
| C12P 19/02 | (2006.01) |
| C12P 19/14 | (2006.01) |
| C13K 1/00 | (2006.01) |
| C12N 1/16 | (2006.01) |
| C07C 51/367 | (2006.01) |
| C07C 59/01 | (2006.01) |

(52) U.S. Cl.
CPC ............. *C12P 7/42* (2013.01); *C07C 51/377* (2013.01); *C12P 19/02* (2013.01); *C12P 19/14* (2013.01); *C13K 1/00* (2013.01)

(58) Field of Classification Search
None
See application file for complete search history.

(56) References Cited

U.S. PATENT DOCUMENTS

| | | | |
|---|---|---|---|
| 7,405,063 B2 | 7/2008 | Eirich et al. | |
| 8,158,391 B2 | 4/2012 | Gross et al. | |
| 2015/0336999 A1 | 11/2015 | Jourdier et al. | |
| 2017/0369910 A1 | 12/2017 | Tsakraklides et al. | |
| 2018/0105848 A1 | 4/2018 | Shaw et al. | |

FOREIGN PATENT DOCUMENTS

JP    2011253226 A    6/2013

OTHER PUBLICATIONS

Geys et al. (Increasing Uniformity of Biosurfactant Production in Starmerella bombicola via the Expression of Chimeric Cytochrome P450s, Colloids Interfaces, 2018, 2, 42, pp. 1-13).*
Bordeaux et al., "Catalytic, Mild, and Selective Oxyfunctionalization of Linear Alkanes: Current Challenges", Angew. Chem. Int. Ed., 51 (2012) 10712-10723.
De Graeve et al., "Starmerella bombicola, an industrially relevant, yet fundamentally underexplored yeast", FEMS Yeast Research, 18 (2018) 1-13.
Schaffer et al., "Biocatalytic and Fermentative Production of alpha,omega-Bifunctional Polymer Precursors", Organic Process Research & Development, 18 (2014) 752-766.
Rau et al., "Sophorolipids: a source for novel compounds", Industrial Crops and Products, 13 (2001) 85-92.

* cited by examiner

*Primary Examiner* — Suzanne M Noakes
*Assistant Examiner* — Jae W Lee
(74) *Attorney, Agent, or Firm* — SHOOK, HARDY & BACON, L.L.P.

(57) ABSTRACT

Hydroxycarboxylic acids may be biosynthesized from a carbonaceous feedstock and then isolated through forming and subsequently hydrolyzing an intermediate sophorolipid. After biosynthesizing a hydroxycarboxylic acid in a cell culture medium or otherwise providing a hydroxycarboxylic acid in a first aqueous medium, the hydroxycarboxylic acid and glucose may be converted into at least one sophorolipid by a suitable microorganism or an enzyme cocktail. The at least one sophorolipid may be then be separated from the cell culture medium or first aqueous medium and then hydrolyzed in a second aqueous medium to form the hydroxycarboxylic acid and glucose as free components separate from the cell culture medium or first aqueous medium. The hydroxycarboxylic acid is present as a phase separate from the second aqueous medium and the glucose remains in the second aqueous medium.

23 Claims, 8 Drawing Sheets

FORMATION AND ISOLATION OF HYDROXYCARBOXYLIC ACIDS VIA A SOPHOROLIPID INTERMEDIATE

FIELD OF THE INVENTION

The present disclosure relates to biosynthesis of hydroxycarboxylic acids and purification thereof.

BACKGROUND OF THE INVENTION

Hydroxy fatty acids, also referred to herein as hydroxycarboxylic acids or hydroxyacids, are versatile materials that may be used for producing a number of different types of products, such as resins, polyamides (nylons), polyesters, lubricants, biopolymers, and surfactants. Although hydroxycarboxylic acids have many potential uses, the breadth of available structural diversity within long-chain hydroxycarboxylic acids (e.g., $C_{8+}$, particularly $C_{16+}$) remains somewhat sparse, since these molecules can be fairly complicated to synthesize through conventional chemical syntheses. Long-chain hydroxycarboxylic acids can be especially difficult to access through conventional chemical syntheses due to the presence of multiple sites having similar chemical reactivity. For these reasons, conventional chemical syntheses of hydroxycarboxylic acids face many challenges, such as limited conversion rates and low yields, poor selectivity for the position and/or stereochemistry of functionalization (e.g., introduced hydroxyl groups or other moieties), harsh reaction conditions, difficult separations, high energy input rates, and use of expensive and potentially environmentally unfriendly oxidants (e.g., t-butylhydroperoxide and others).

Interest in biological-based syntheses (biosyntheses) has risen in recent years due to their potential to afford high yields and good regioselectivity and/or stereoselectivity for introducing a specified type of functionalization. In addition, biosyntheses may be considerably more environmentally friendly and have lower energy input requirements compared to their chemical counterparts. Despite their advantages, biosyntheses have yet to realize their full potential due to the sometimes considerably more difficult product purification that may result in comparison to conventional chemical syntheses. It also may be difficult to identify a suitable microorganism for carrying out a biological synthesis of a specified synthetic target in sufficiently high yield and purity and with good regioselectivity and/or stereoselectivity, particularly starting from a low-cost feedstock material. These issues may be particularly prevalent when synthesizing hydroxycarboxylic acids via biological-based syntheses.

SUMMARY OF THE INVENTION

In some embodiments, methods of the present disclosure may comprise obtaining at least one sophorolipid; and hydrolyzing the at least one sophorolipid in an aqueous medium to form glucose and at least one hydroxycarboxylic acid as free components, the at least one hydroxycarboxylic acid being present as a phase separate from the aqueous medium and the glucose remaining in the aqueous medium.

In some or other various embodiments, methods of the present disclosure may comprise biosynthesizing a hydroxycarboxylic acid in a cell culture medium comprising glucose by exposing a carbonaceous feedstock to a microorganism capable of forming at least one sophorolipid; forming at least one sophorolipid from the hydroxycarboxylic acid and glucose within the cell culture medium; separating the at least one sophorolipid from the cell culture medium; and after separating the at least one sophorolipid from the cell culture medium, hydrolyzing the at least one sophorolipid in an aqueous medium to form the hydroxycarboxylic acid and glucose as free components separate from the cell culture medium; wherein the hydroxycarboxylic acid is present as a phase separate from the aqueous medium and the glucose remains in the aqueous medium.

In still more specific embodiments, providing a normal alkane to a cell culture medium comprising glucose; biosynthesizing a hydroxycarboxylic acid in the cell culture medium by exposing the normal alkane to a microorganism capable of forming the hydroxycarboxylic acid and converting the hydroxycarboxylic acid and glucose into at least one sophorolipid; forming the at least one sophorolipid within the cell culture medium, at least a portion of the at least one sophorolipid comprising an acidic sophorolipid secreted from the microorganism into the cell culture medium and collecting as a lower layer within the cell culture medium; separating the at least one sophorolipid from the cell culture medium; and after separating the at least one sophorolipid from the cell culture medium, hydrolyzing the at least one sophorolipid in an aqueous medium to form the hydroxycarboxylic acid and glucose as free components separate from the cell culture medium; wherein the hydroxycarboxylic acid is present as a phase separate from the aqueous medium and the glucose remains in the aqueous medium.

In some or other embodiments, methods of the present disclosure may comprise: exposing a hydroxycarboxylic acid to an enzyme cocktail in a first aqueous medium, the enzyme cocktail comprising at least glucosyltransferase I, glucosyltransferase II, and lactone esterase and the first aqueous medium comprising glucose; forming at least one sophorolipid within the first aqueous medium; wherein the at least one sophorolipid collects as a lower layer within the first aqueous medium; separating the at least one sophorolipid from the first aqueous medium; and after separating the at least one sophorolipid from the first aqueous medium, hydrolyzing the at least one sophorolipid in a second aqueous medium to form the hydroxycarboxylic acid and glucose as free components separate from the first aqueous medium; wherein the hydroxycarboxylic acid is present as a phase separate from the second aqueous medium and the glucose remains in the second aqueous medium.

In still other embodiments, compositions of the present disclosure may comprise: a functionalized hydroxycarboxylic acid represented by Structure 4 or a reaction product thereof

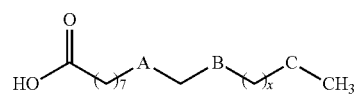

Structure 4 wherein: x is 0, 2, 4, 6, 8 or 10, A is cis —CH=CH—, —CH$_2$—CH$_2$—, —CH—CH(CH$_3$)—, or —CH—CH(OH)—; B and C are independently —CH$_2$— or —CH(OH)—, with provisos that 1) one of B and C is —CH$_2$— and one of B and C is —CH(OH)—, provided A is not —CH—CH(OH)—, and if A is —CH—CH(OH)—, both B and C are —CH$_2$—, 2) A, B, C and x are chosen such that A, B, C and x are not simultaneously cis —CH=CH—, —CH(OH)—, —CH$_2$—, and 4, respectively, and 3) A, B and C are chosen such that A, B and C are not simultaneously cis —CH═CH—, —CH$_2$—, and —CH(OH)—, respectively.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION OF THE INVENTION

Figure 1:
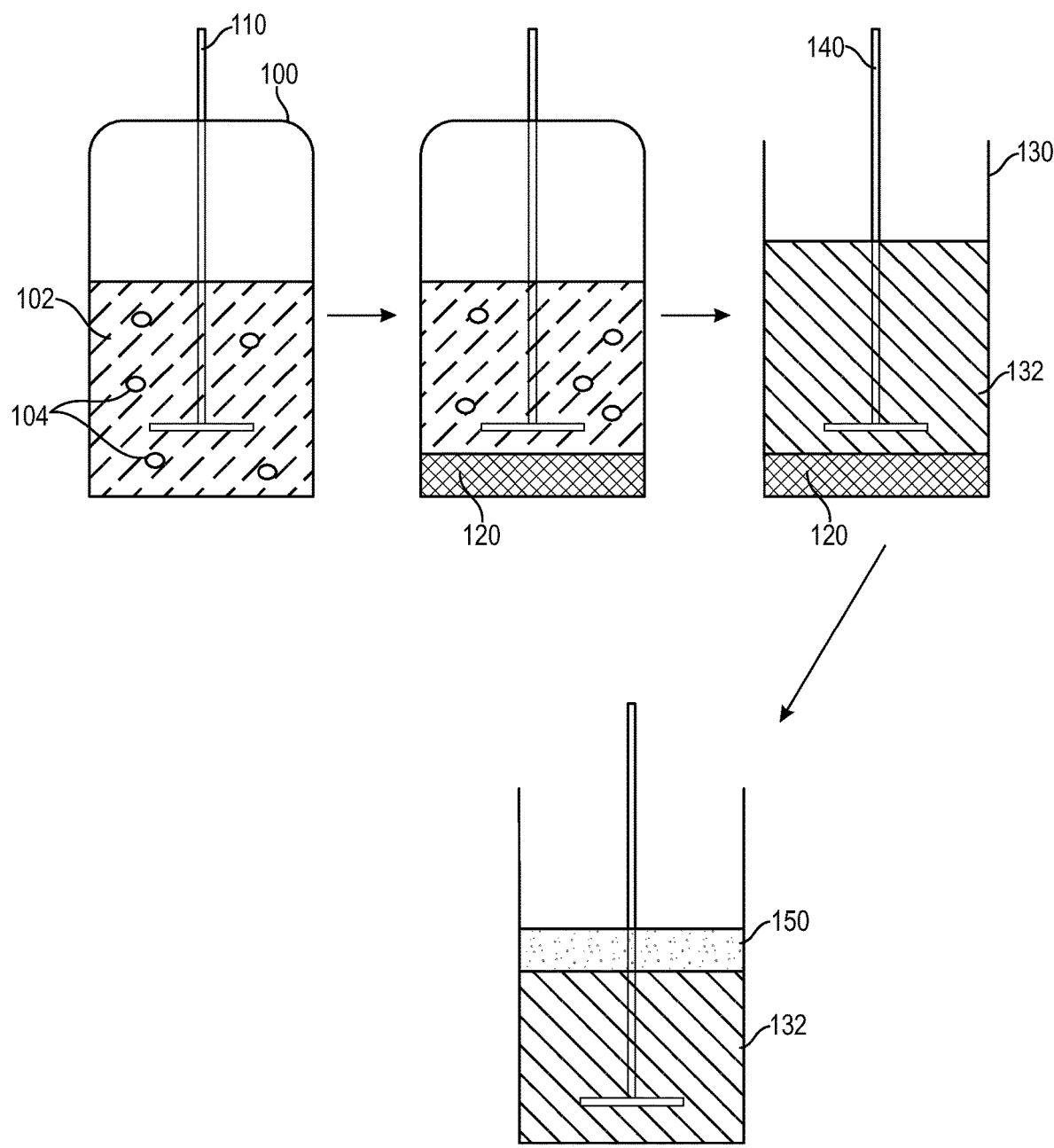
FIG. 1 shows an illustrative diagram of the hydroxycarboxylic acid formation and separation processes disclosed herein.

The present disclosure generally relates to biosyntheses and, more specifically, to biosyntheses of hydroxycarboxylic acids and purification thereof.

As discussed above, hydroxycarboxylic acids, particularly long-chain hydroxycarboxylic acids ($C_{8+}$, particularly $C_{16+}$, referring to the main carbon chain length), are a desirable class of molecules that may have a number of downstream uses. However, long-chain hydroxycarboxylic acids, especially substituted long-chain hydroxycarboxylic acids, may be difficult to synthesize in appreciable yields and purity using existing chemical synthesis routes. Current biosynthetic approaches for synthesizing long-chain hydroxycarboxylic acids fail to rectify these issues completely, particularly using low-cost carbonaceous feedstocks.

The present disclosure addresses these deficiencies by providing biosynthetic approaches for producing hydroxycarboxylic acids, including selectively functionalized variants thereof, that may proceed from low-cost carbonaceous feedstocks and may be readily purified. In particular, the present disclosure describes biosyntheses of hydroxycarboxylic acids proceeding through a sophorolipid intermediate that may be readily isolated, thereby allowing a free hydroxycarboxylic acid to be obtained in a relatively pure state. In particular, process configurations disclosed herein may utilize a microorganism capable of converting a hydroxycarboxylic acid into at least one sophorolipid that may be readily separated from other biologically produced compounds, a cell culture medium, or the like to allow the hydroxycarboxylic acid to be obtained subsequently in a relatively pure state. The at least one sophorolipid may be an acidic sophorolipid, a lactonic sophorolipid, or any combination thereof. Various yeast species are capable of forming hydroxycarboxylic acids and subsequently converting the hydroxycarboxylic acids into sophorolipids starting from low-cost carbonaceous feedstocks and glucose, as described in further detail hereinafter. Alternately, an unfunctionalized carboxylic acid (i.e., not bearing a hydroxyl group) or a hydroxycarboxylic acid obtained from another source, may be exposed to the yeast species to facilitate hydroxycarboxylic acid purification via a sophorolipid intermediate according to the disclosure herein.

Yeast species may natively produce a hydroxycarboxylic acid with a terminal carboxylic acid group, a carbon-carbon unsaturation at C8 and C9 relative to the carboxylic acid group, and a hydroxyl group at the ω-1 position. Although such hydroxycarboxylic acids may be produced natively by yeast species, they are not believed to have been further purified in accordance with the disclosure herein.

In addition to the foregoing advantages, yeast species may be readily genetically modified to change the enzymes they produce, thereby allowing the functionalization pattern upon the hydroxycarboxylic acid to be changed, often in a selective way. When synthesizing hydroxycarboxylic acids chemically, in contrast, it may be difficult to control the extent and/or position of functionalization. Chemical synthesis yields may also be low, and certain hydroxycarboxylic acid isomers may be very difficult to produce. Hydroxycarboxylic acids produced using a genetically modified yeast species may include one or more of the following features: methyl branching in a specified position, removal of the carbon-carbon unsaturation, and/or controllable alteration of the hydroxyl group position. Enzymatic transformations that may be suitable for producing these types of hydroxycarboxylic acid alterations are described in greater detail hereinafter. Genetic modification techniques suitable for promoting production of enzymes capable of performing such synthetic transformations are known in the art. Certain long-chain hydroxycarboxylic acid functionalization patterns accessible through the disclosure herein may otherwise be unknown or difficult to access through conventional chemical syntheses.

More specifically, methods of the present disclosure may form at least one sophorolipid in a cell culture medium using a suitable yeast strain. The yeast strain may then secrete the at least one sophorolipid into the cell culture medium as one or more acidic sophorolipids, where the one or more acidic sophorolipids may undergo subsequent conversion into one or more lactonic sophorolipids. Either acidic or lactonic sophorolipids may then separate from the cell culture medium as an immiscible layer, specifically a lower layer. The immiscible layer comprising the at least one sophorolipid may then be separated from the cell culture medium and undergo chemical and/or enzymatic hydrolysis in an aqueous medium to release the hydroxycarboxylic acid in a purified, free form. Specifically, the hydroxycarboxylic acid may form an upper layer upon the aqueous medium following hydrolysis. Glucose may also be released following hydrolysis of the at least one sophorolipid, with the glucose remaining in the aqueous phase. Advantageously, the glucose released from the at least one sophorolipid may be recycled to the cell culture medium to promote formation of additional quantities of the at least one sophorolipid using the yeast strain. Accordingly, hydroxycarboxylic acid formation and purification according to the disclosure herein may be at least partially closed loop in nature.

Although the processes disclosed herein may be favorably conducted using whole cells, such that at least one acidic sophorolipid is secreted by a microorganism (e.g., yeast) into a cell culture medium and at least partially converted into a lactonic sophorolipid extracellularly, it is to be appreciated that isolated enzymes may be used similarly for conducting at least a portion of the chemical transformations disclosed herein. Further, it is to be appreciated that not all of the enzymatic transformations disclosed herein necessarily take place for a particular carbonaceous feedstock. For example, oxidized hydrocarbon variants may be used similarly to saturated carbonaceous feedstocks, with the oxidized hydrocarbon variants entering an enzymatic processing chain at a more downstream location than the corresponding saturated carbonaceous feedstock.

Finally, the hydroxycarboxylic acids produced according to the present disclosure may be accessed in amounts and/or purities sufficient to support various types of commercial products, which may be otherwise inaccessible using conventional chemical syntheses. Hydroxycarboxylic acid structures inaccessible or not easily accessible via conventional chemical syntheses may also be realized using the disclosure herein. Thus, the combination of scale, purity and synthetic flexibility may be particularly advantageous when forming hydroxycarboxylic acids according to the disclosure herein and reaction products and/or formulations produced therefrom.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A" and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$," refers to a hydrocarbon or a hydrocarbyl group having n carbon atom(s) per molecule or group, wherein n is a positive integer. Such hydrocarbons or hydrocarbyl groups may be one or more of linear, branched, cyclic, acyclic, saturated, unsaturated, aliphatic, or aromatic.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbyl groups include, but are not limited to, functional groups such as O, S, S=O, S(=O)$_2$, NO$_2$, F, Cl, Br, I, NR$_2$, OR, SeR, TeR, PR$_2$, AsR$_2$, SbR$_2$, SR, BR$_2$, SiR$_3$, GeR$_3$, SnR$_3$, PbR$_3$, where R is a hydrocarbyl group or H. Suitable hydrocarbyl groups may include alkyl, alkenyl, alkynyl, aryl, heteroaryl, cycloalkyl, cycloalkenyl, heterocyclyl, and the like, any of which may be optionally substituted.

The terms "saturated" or "saturated hydrocarbon" refer to a hydrocarbon or hydrocarbyl group in which all carbon atoms are bonded to four other atoms or bonded to three other atoms with one unfilled valence position thereon.

The terms "unsaturated" or "unsaturated hydrocarbon" refer to a hydrocarbon or hydrocarbyl group in which one or more carbon atoms are bonded to less than four other atoms, optionally with one unfilled valence position on the one or more carbon atoms.

The term "carbon-carbon" unsaturation refers to a double or triple bond between carbon atoms.

The term "alkyl" refers to a hydrocarbyl group having no unsaturated carbon-carbon bonds, and which may be optionally substituted.

The term "alkenyl" refers to a hydrocarbyl group having a carbon-carbon double bond, and which may be optionally substituted. The terms "alkene" and "olefin" may be used synonymously herein. Similarly, the terms "alkenic" and "olefinic" may be used synonymously herein. Unless otherwise noted, all possible geometric and positional isomers are encompassed by these terms. Preferably, alkenyl groups formed biosynthetically in the hydroxycarboxylic acids disclosed here are cis olefins.

The term "alpha olefin" refers to a hydrocarbon compound having a terminal double bond. The term "linear alpha olefin" refers to an alpha olefin having a substantially unbranched alkyl group appended to the terminal double bond.

The term "germinal substituted olefin" refers to an olefin having two of the same substitution upon the same carbon atom.

The term "vicinal substituted olefin" refers to an olefin having two of the same substitution upon adjacent carbon atoms.

The term "vinylidene olefin" refers to an olefin bearing two hydrogen atoms upon C-1 of the olefin and two hydrocarbyl groups upon C-2 of the olefin.

The terms "alkanol," "alkenol" and "alkynol" respectively refer to an alkane, alkene or alkyne containing an alcohol moiety.

The terms "alkanoic acid," "alkenoic acid" and "alkynoic acid" respectively refer to an alkane, alkene or alkyne containing a carboxylic acid moiety. The corresponding esters are referred to similarly.

The terms "aromatic" and "aromatic hydrocarbon" refer to a hydrocarbon or hydrocarbyl group having a cyclic arrangement of conjugated pi-electrons that satisfy the Hückel rule. The term "aryl" is equivalent to the term "aromatic" as defined herein. The term "aryl" refers to both aromatic compounds and heteroaromatic compounds, either of which may be optionally substituted. Both mononuclear and polynuclear aromatic compounds are encompassed by these terms. Aromatic rings within a mononuclear or polynuclear aromatic compound may be fused or unfused.

The terms "linear," "linear hydrocarbon" and "linear alkyl group" refer to a hydrocarbon, hydrocarbyl or alkyl group having a continuous carbon chain without side chain branching, in which the continuous carbon chain may be optionally substituted with heteroatoms or heteroatom groups.

The terms "branch," "branched," "branched hydrocarbon" and "branched alkyl" refer to a hydrocarbon, hydrocarbyl or alkyl group having a linear main carbon chain in which a hydrocarbyl side chain extends from the linear main carbon chain. Optional heteroatom substitution may be present in the linear main carbon chain or in the hydrocarbyl side chain.

The term "hydroxycarboxylic acid" refers to a compound containing a carboxylic acid group and an alcohol hydroxyl group.

The term "sophorolipid" refers to a disaccharide comprising two glycosidically linked glucose units (thereby defining the disaccharide sophorose) and a hydroxycarboxylic acid unit glycosidically linked to the terminal glucose unit of the disaccharide. This linear arrangement of sophorose and the hydroxycarboxylic acid has a free carboxylic acid group and may be referred to as an "an acidic sophorolipid" (Structure 1). The free carboxylic acid group may also undergo cyclization with the other glucose unit of the disaccharide to form a lactonic structure and may be referred to as a "lactonic sophorolipid" (Structure 2).

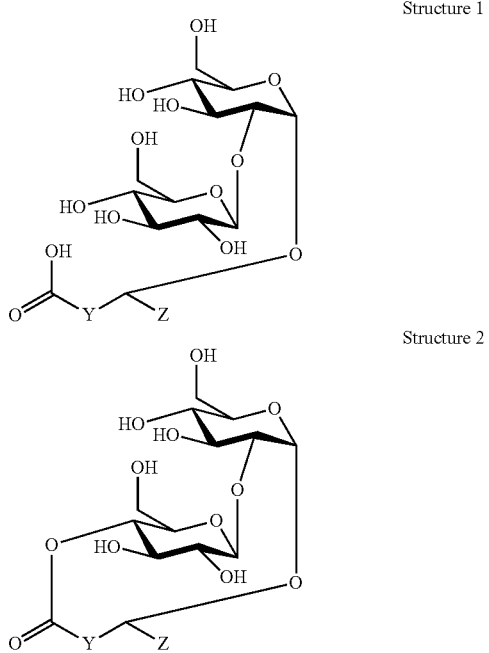

Structure 1

Structure 2

In Structures 1 and 2, Y and Z are both hydrocarbyl groups.

The terms "ω" or "ω position" refer to the location upon the carbon chain of a hydroxycarboxylic acid that is most remote from a carboxylic acid group of the hydroxycarboxylic acid. The terms "ω-1" or "ω-1 position" refer to the next most remote location.

The term "glycosidic bond" refers to a covalent bond between a hemiacetal or hemiketal group of a first monosaccharide and a hydroxyl group of a second monosaccharide.

The term "hydrolyzing" refers to cleavage of an ester bond and/or a glycosidic bond.

The term "free component(s)" refers to a substance or substances that is/are not part of sophorolipid.

The term "cell culture medium" refers to a liquid medium formulated to support the growth of a microorganism in the presence of one or more suitable nutrient sources.

The term "in a/the cell culture medium" refers to processes taking place intracellularly or extracellularly within a cell culture medium.

A sophorolipid, specifically an acidic sophorolipid, may be secreted by a suitable microorganism into a cell culture medium. Subsequent formation of a lactonic sophorolipid may then occur. As the sophorolipid is secreted and subsequently lactonized, a biphasic mixture may form, in which the sophorolipid separates as a lower layer of the biphasic mixture. Once the lower layer has been separated from the cell culture medium, the sophorolipid may then be hydrolyzed according to the disclosure herein to release the hydroxycarboxylic acid as a free component. The hydroxycarboxylic acid may form as a phase separate from an aqueous medium in which the hydrolysis is conducted, thereby allowing isolation of the hydroxycarboxylic acid to take place.

The foregoing concepts are further illustrated in FIG. 1. FIG. 1 shows an illustrative diagram of the hydroxycarboxylic acid formation and separation processes disclosed herein. As shown, bioreactor 100 contains cell culture medium 102, which includes microorganisms 104 and a carbonaceous feedstock (not shown) and glucose (not shown). Cell culture medium 102 may be stirred with stirrer 110, if desired. Under suitable conditions, microorganisms 102 secrete at least one sophorolipid, which eventually separates as lower sophorolipid layer 120. Lower sophorolipid layer 120 may then be removed from bioreactor 100 (e.g., by draining, siphoning, pipetting or the like), thereby achieving separation from cell culture medium 102, and transferred to vessel 130. Aqueous medium 132, which may be an aqueous acid or contain an enzyme capable of hydrolyzing the at least one sophorolipid, is then contacted with the at least one sophorolipid to promote hydrolysis. Stirring may be conducted with stirrer 140, if desired. Following hydrolysis, the resulting hydroxycarboxylic acid is immiscible with aqueous medium 132 and is less dense than aqueous medium 132. Thus, upper hydroxycarboxylic acid layer 150 may collect following hydrolysis. After removing aqueous medium 132, upper hydroxycarboxylic acid layer 150 may be removed for further reactions or formulation.

Although FIG. 1, shows the hydroxycarboxylic acid being formed in bioreactor 100 and subsequently converted into at least one sophorolipid, it is to be appreciated that the hydroxycarboxylic acid or the at least one sophorolipid may be sourced separately and subjected to the processes disclosed herein. For example, a hydroxycarboxylic acid may be obtained from another source and exposed to microorganisms 104 in bioreactor 100 for converting the hydroxycarboxylic acid into at least one sophorolipid, which may subsequently collect as lower sophorolipid layer 120. Similarly, a separately sourced sophorolipid may be introduced into vessel 130 for hydrolysis and subsequent separation without being produced directly in an upstream bioreactor.

Accordingly, methods of the present disclosure may comprise obtaining at least one sophorolipid, and hydrolyzing the at least one sophorolipid in an aqueous medium to form glucose and at least one hydroxycarboxylic acid as free components, with the at least one hydroxycarboxylic acid being present as phase separate from the aqueous medium and the glucose remaining in the aqueous medium. Specifically, the at least one hydroxycarboxylic acid may be present as the upper phase of a biphasic mixture, thereby allowing separation of the at least one hydroxycarboxylic acid to take place from the aqueous medium. The at least one sophorolipid may be obtained from a cell culture medium (e.g., as the lower layer of a biphasic mixture) following formation (biosynthesis) of the at least one sophorolipid by a suitable microorganism in the presence of a suitable carbonaceous feedstock and glucose. In the case of a yeast being the microorganism, the cell culture medium may, in a non-limiting example, comprise 100 g/L glucose, 10 g/L yeast extract, and 1 g/L urea adjusted to pH 5.5-6.0 with HCl. Following separation of the at least one sophorolipid from the cell culture medium, hydrolysis to form at least one hydroxycarboxylic acid and glucose as free components may take place.

Alternately, at least one sophorolipid may be obtained from a location other than the cell culture medium, with the at least one sophorolipid being hydrolyzed as above to afford at least one hydroxycarboxylic acid and glucose as free components. The at least one sophorolipid obtained from another location may be an acidic sophorolipid, a lactonic sophorolipid, or any combination thereof. Conditions for forming, separating, and hydrolyzing the at least one sophorolipid are provided in further detail hereinbelow.

As such, more specific examples of the methods disclosed herein may comprise: biosynthesizing a hydroxycarboxylic acid in a cell culture medium comprising glucose by exposing a carbonaceous feedstock to a microorganism capable of forming at least one sophorolipid, forming at least one sophorolipid from the hydroxycarboxylic acid and glucose within the cell culture medium, separating the at least one sophorolipid from the cell culture medium (e.g., as a lower layer of a biphasic mixture), and after separating the at least one sophorolipid from the cell culture medium, hydrolyzing the at least one sophorolipid in an aqueous medium to form the hydroxycarboxylic acid and glucose as free components separate from the cell culture medium. In particular, the hydroxycarboxylic acid is present as a phase separate from the aqueous medium (e.g., as an upper layer of a biphasic mixture) and the glucose remains in the aqueous medium.

Thus, the present disclosure allows processing of hydroxycarboxylic acids and sophorolipids formed therefrom to take place based on density changes occurring following sophorolipid formation and hydrolysis. Namely, following sophorolipid formation, the at least one sophorolipid is more dense than water, thereby allowing ready separation of the at least one sophorolipid from the cell culture medium to take place as an immiscible lower phase. Following hydrolysis, the at least one hydroxycarboxylic acid remains immiscible but is now less dense than water, thereby allowing separation from the aqueous medium in which hydrolysis is conducted to take place. Specifically, separation of the hydroxycarboxylic acid may take place by collection of an upper phase separate from the aqueous medium in which hydrolysis took place.

The at least one sophorolipid produced according to the disclosure herein may comprise an acidic sophorolipid, a lactonic sophorolipid, or any combination thereof. When the at least one sophorolipid is produced directly in a cell culture medium, a microorganism may produce and then secrete at least one acidic sophorolipid into the cell culture medium. The at least one acidic sophorolipid may undergo subsequent cyclization into a lactonic sophorolipid within the cell culture medium. It is to be appreciated that a given sophorolipid does not need to undergo complete conversion into a lactonic sophorolipid prior to being hydrolyzed according to the disclosure herein.

A range of microorganisms, particularly yeasts, may be capable of converting a carbonaceous feedstock into a hydroxycarboxylic acid and subsequently into the at least one sophorolipid for processing according to the disclosure herein. Yeasts may be particularly suitable microorganisms for use in the disclosure herein, since they are usually cultured easily and may be readily genetically modified, such as to encode production of one or more enzymes for promoting a desired type of functionalization not carried out by the native enzyme, as discussed further below. Suitable yeasts, which may be unmodified or further genetically modified, for use in the disclosure herein may include, for example, *Starmerella bombicola* (*Candida bombicola*), *Candida albicans*, *Candida floricola*, *Candida apicola*, *Candida riodocensis*, *Candida stellate*, *Candida zemplinina*, *Candida stellata*, *Candida lactis-condensi*, *Candida cellae*, *Candida etchellsii*, *Candida floris*, *Candida sorbosivorans*, *Candida geochares*, *Candida magnoliae*, *Candida vaccinii*, *Candida apis*, *Candida gropengiesseri*, *Candida bombiphila*, *Candida batistae*, *Candida rugosa*, *Candida kuoi*, *Candida tropicalis*, *Cryptococcus* sp., *Torulopsis petrophilum*, *Pichia anornala*, *Rhodotorula bogoriensis*, *Rhodotorula muciliginosa*, *Wickerhamiella domercqiae*, *Cyberlindnera samutprakarnensis*, or any combination thereof. *Starmerella bombicola* (*Candida bombicola*) may be particularly suitable yeasts for forming sophorolipids and hydroxycarboxylic acids therefrom according to the disclosure herein.

A wide variety of carbonaceous feedstocks may be converted into a hydroxycarboxy carboxylic acid according to the disclosure herein. Suitable carbonaceous feedstocks may include, for example, an alkane, an alkene, a cis olefin, a trans olefin, a geminal substituted olefin, a vicinal substituted olefin, an alpha olefin, a vinylidene olefin, an alkyne, an alkanol, an alkenol, an alkynol, an alkanoic acid, an alkenoic acid, an alkynoic acid, an alkanoic ester, an alkenoic ester, an alkynoic ester, crude oil, a crude oil component, waste oil, vegetable oil, a fat, a lipid, or any combination thereof.

Advantageously, yeasts may preferentially process any of the foregoing carbonaceous feedstocks into a $C_{16}$ or $C_{18}$ hydroxycarboxylic acid and subsequently form at least one sophorolipid therefrom, which may be further processed according to the disclosure herein. $C_{16}$ or $C_{18}$ hydroxycarboxylic acids are the preferred chain lengths produced by the yeasts disclosed herein. Carbonaceous feedstocks shorter than $C_{16}$ may undergo at least partial lengthening into a $C_{16}$ or $C_{18}$ main chain length, and those longer than $C_{18}$ may undergo at least partial shortening into this carbon chain length range in some instances. The nature of the carbonaceous feedstock and its initial chain length may determine the extent to which chain lengthening or chain shortening takes place in a given instance. Although $C_{16}$ or $C_{18}$ hydroxycarboxylic acids are preferred, a broader range of $C_{14}$-$C_{24}$ hydroxycarboxylic acids may form in certain instances, again being dependent at least to some degree upon the chosen carbonaceous feedstock and its initial chain length.

Figure 2:
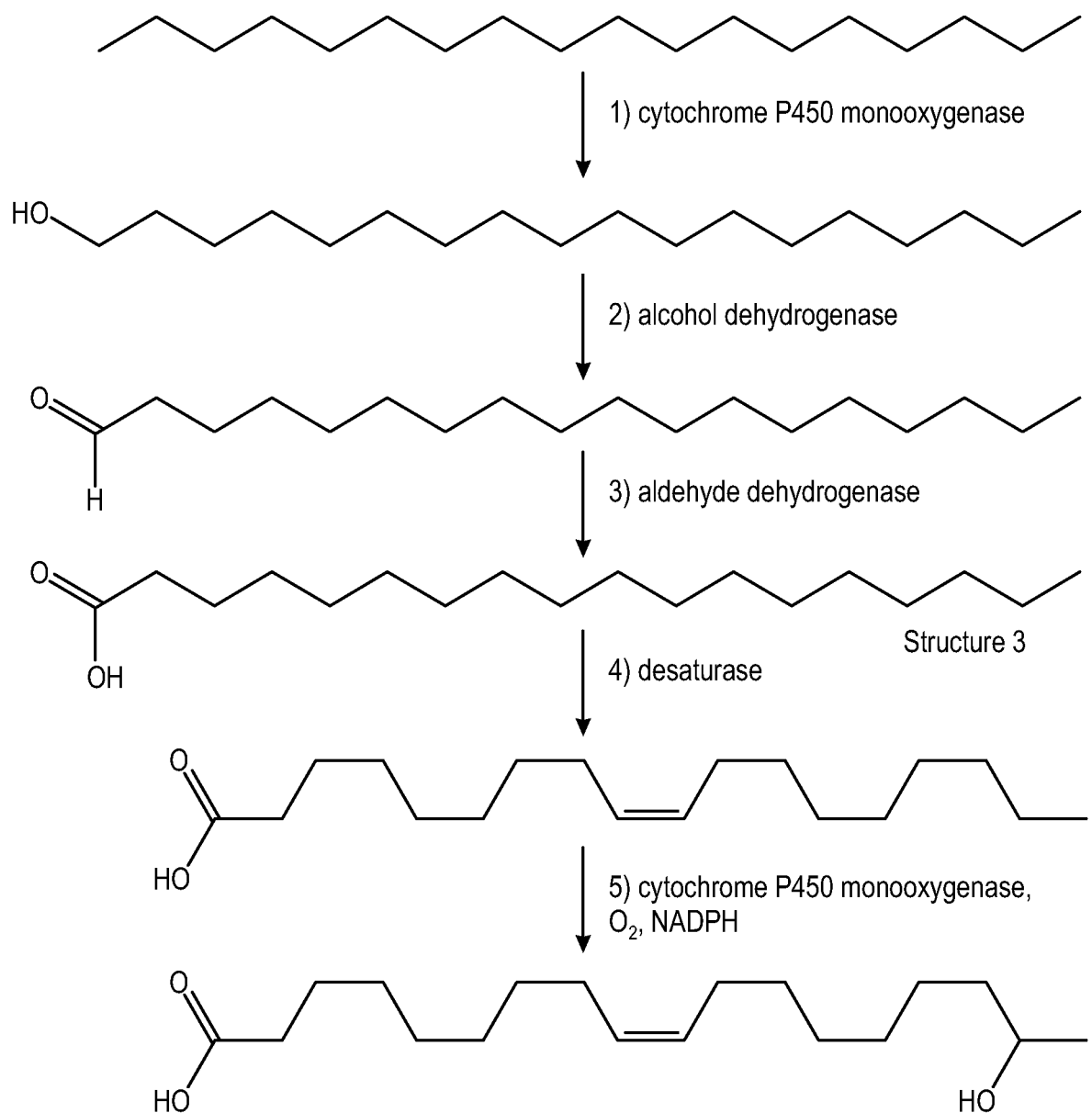
FIG. 2 illustrates the sequence of enzymatic reactions that an illustrative alkane, octadecane, may undergo to form a hydroxycarboxylic acid in a yeast that has not been genetically modified.

It is to be appreciated that the above carbonaceous feedstocks may undergo various enzymatically promoted chemical transformations to form a hydroxycarboxylic acid according to the disclosure herein. FIG. 2 illustrates the sequence of enzymatic reactions that an illustrative alkane, octadecane, may undergo to form a hydroxycarboxylic acid in a yeast that has not been genetically modified. Alkanes, particularly normal alkanes, may undergo the greatest number of enzymatic transformations in the enzymatic pathway, since these unfunctionalized carbonaceous feedstocks need to undergo enzymatic reactions to introduce both a hydroxyl group and a carboxylic acid group, in addition to forming a carbon-carbon unsaturation between C-9 and C-10. Other carbonaceous feedstocks initially bearing a carboxylic acid, an alcohol, or carbon-carbon unsaturation may not undergo one or more of the enzymatic transformations that alkanes undergo. That is, depending on the functionalization present and its position, other carbonaceous feedstocks may enter the sequence of enzymatic reactions at a more downstream point.

Referring to FIG. 2, octadecane may undergo oxidation at one of the terminal carbon atoms under cytochrome P450 monooxygenase mediation to form a primary alcohol. The primary alcohol, in turn, may then be oxidized to an aldehyde and carboxylic acid under alcohol dehydrogenase and aldehyde dehydrogenase mediation, respectively, to afford stearic acid (Structure 3). Stearic acid (Structure 3) is also formed in the enzymatic pathways promoted by genetically modified yeasts to form other variants of hydroxycarboxylic acids, as discussed further below. Once stearic acid has formed intracellularly within the yeast cells, carbon-carbon unsaturation is introduced under desaturase mediation between C-9 and C-10 with respect to the carboxylic acid group. Native yeasts are capable of introducing such carbon-carbon unsaturation within the hydroxycarboxylic acid or a precursor thereof. Finally, a secondary alcohol is introduced at the ω-1 position under cytochrome P450 monooxygenase mediation in the presence of $O_2$ and NADPH. The carbon-carbon unsaturation, if present, and/or the location of the hydroxyl group may differ in genetically modified yeasts, as discussed further hereinbelow.

The hydroxycarboxylic acid formed in accordance with FIG. 2 may then be converted into at least one sophorolipid through additional enzymatically promoted reactions. Specifically, the hydroxycarboxylic acid shown in FIG. 2 may be subsequently converted into a glucolipid upon interacting the hydroxycarboxylic acid with glucose (specifically glucose activated with uridine diphosphate; UDP-glucose) under glucosyltranferase I mediation. A second glucose unit may then be added similarly to form an acidic sophorolipid (Structure 1, X=$(CH_2)_7$(cis-CH=CH)$(CH_2)_6$, Y =$CH_3$) under glucosyltransferase II mediation. At this point, the acidic sophorolipid may be secreted from the yeast into the cell culture medium for further extracellular modification. Thereafter, the acidic sophorolipid may be converted extracellularly under lactone esterase mediation into the corresponding lactonic sophorolipid. The at least one sophorolipid, which may be an acidic sophorolipid, a lactonic sophorolipid or any combination thereof, may then be separated (harvested) from the cell culture medium so that hydrolytic removal of the sophorose disaccharide may take place to release the free hydroxycarboxylic acid.

If effective secretion of the at least one sophorolipid, specifically an acidic sophorolipid, does not take place, the yeast cells may be harvested, with cell lysis then taking place to release the acidic sophorolipid so that further processing can take place. Alternately, cell lysis of the yeast may take place directly in the cell culture medium without first harvesting the yeast cells.

Hydrolysis of the at least one sophorolipid may take place using chemical or enzymatic hydrolysis in an aqueous medium. Enzymatic hydrolysis, which may facilitate 'all-biological' syntheses of hydroxycarboxylic acids may take place by including the enzyme naringinase in the aqueous medium. Chemical hydrolysis, in contrast, may be conducted using an aqueous acid, thereby liberating the hydroxycarboxylic acid in its protonated form, such that the hydroxycarboxylic acid may phase separate as the upper layer of a bilayer mixture. Alternately, hydrolysis may take place under basic conditions followed by acidification to protonate the carboxylate salt otherwise formed. Suitable acids for performing acidic hydrolysis of the at least one acidic sophorolipid may include, for example, sulfuric acid, hydrochloric acid, hydrobromic acid, and the like.

Genetically modified yeasts or other microorganisms capable of forming at least one sophorolipid may change the substitution pattern upon the hydroxycarboxylic acid, as explained hereinafter in reference to FIGS. 3-5.

Methyl substitution and elimination of the carbon-carbon unsaturation in the natively produced hydroxycarboxylic acids may be realized by using a genetically modified yeast that is capable of introducing a methyl branch within the hydroxycarboxylic acid or a precursor thereof, such that at least one methyl branch is introduced onto the carbon chain of the hydroxycarboxylic acid or the precursor thereof. Specifically, suitable yeasts capable of introducing a methyl branch may be genetically modified to produce the enzymes methyltransferase and reductase in order to introduce a methyl branch at C-10, as shown hereinafter in reference to FIG. 3.

Figure 3:
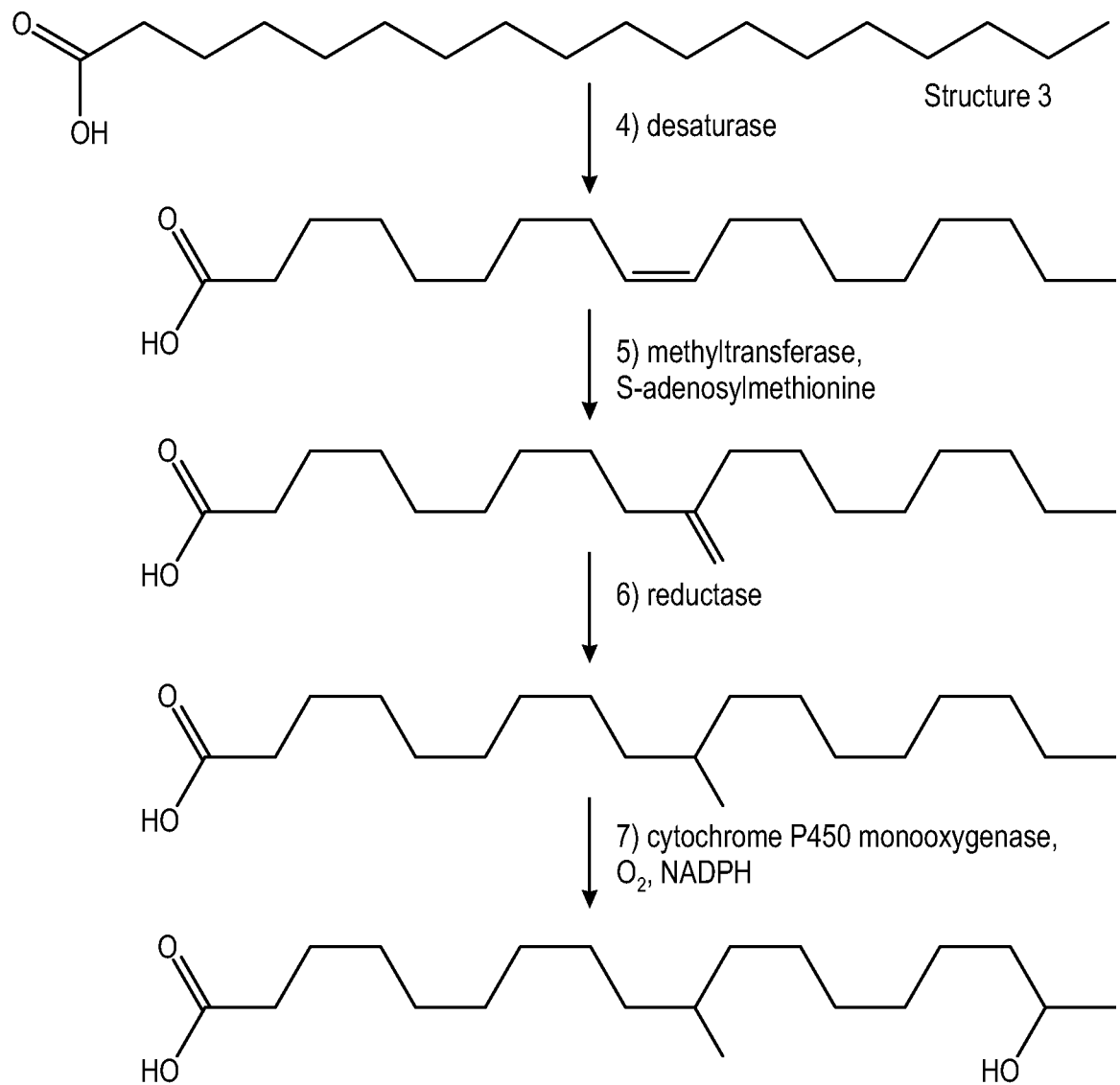
FIG. 3 illustrates a portion of the sequence of enzymatic reactions that an illustrative alkane, octadecane, may undergo to form a C-10 methyl-branched hydroxycarboxylic acid using a genetically modified yeast.

FIG. 3 illustrates a portion of the sequence of enzymatic reactions that an illustrative alkane, octadecane, may undergo to form a C-10 methyl-branched hydroxycarboxylic acid using a genetically modified yeast. The sequence of enzymatic reactions up through the production of stearic acid (Structure 3) is the same as those shown in FIG. 2, and description thereof is not repeated in the interest of brevity. Referring to FIG. 3, desaturase again introduces a double bond between C-9 and C-10 with respect to the carboxylic acid group. Thereafter, the double bond is removed and a methylene group is introduced at C-10 under the mediation of methyltransferase in the presence of S-adenosylmethionine cofactor. The enzyme reductase then promotes reduction of the methylene group to afford the corresponding methyl group at C-10, followed by hydroxyl group introduction at the ω-1 position under cytochrome P450 monooxygenase mediation. Glucolipid and sophorolipid formation may then take place in a manner similar to that described above.

Modification of the hydroxyl group position in the hydroxycarboxylic acid is made possible by using a genetically modified yeast that is capable of introducing a hydroxyl group at a position other than the ω-1 position of the hydroxycarboxylic acid or a precursor thereof. The carbon-carbon unsaturation between C-9 and C-10 may be retained or removed depending on the enzyme used to promote hydroxyl group introduction, as discussed hereinafter.

Genetically modified yeasts may be capable of introducing a hydroxyl group at C-12, with respect to a carboxylic acid group of the hydroxycarboxylic acid. Specifically, suitable yeasts capable of introducing a hydroxyl group at C-12 may retain the carbon-carbon unsaturation between C-9 and C-10 using a heterologous 12-hydroxylase to promote hydroxyl group introduction, as explained hereinafter in reference to FIG. 4.

Figure 4:
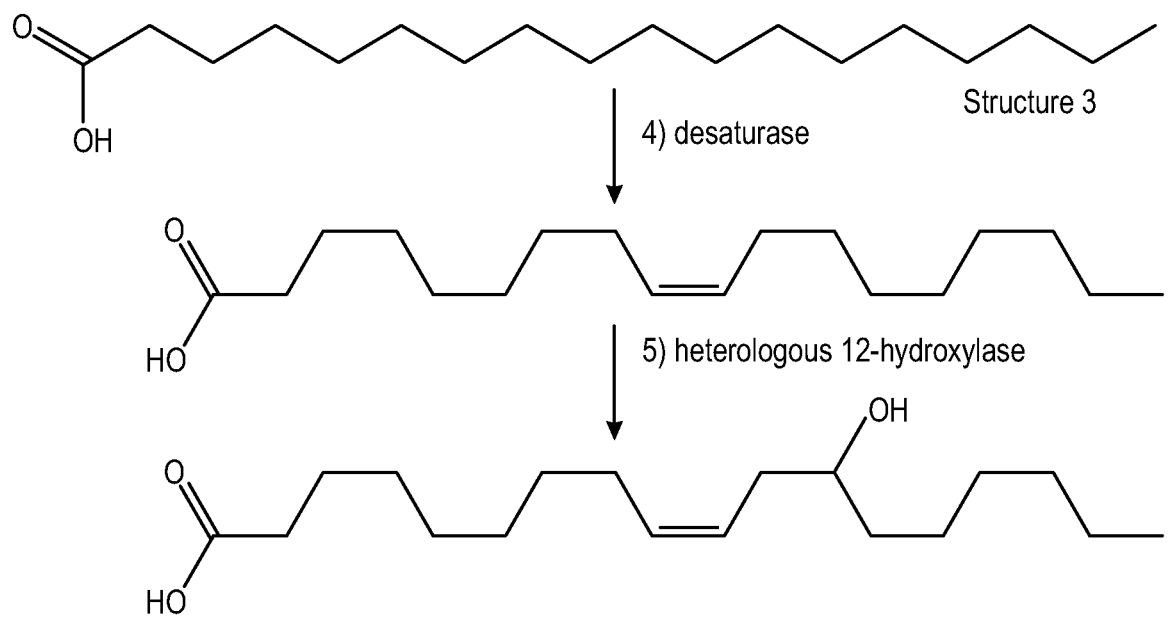
FIG. 4 illustrates a portion of the sequence of enzymatic reactions that an illustrative alkane, octadecane, may undergo to form a C-12 hydroxycarboxylic acid using a genetically modified yeast.

FIG. 4 illustrates a portion of the sequence of enzymatic reactions that an illustrative alkane, octadecane, may undergo to form a C-12 hydroxycarboxylic acid using a genetically modified yeast. The sequence of enzymatic reactions up through the production of stearic acid (Structure 3) is the same as those shown in FIG. 2, and description thereof is not repeated in the interest of brevity. Referring to FIG. 4, desaturase again introduces a double bond between C-9 and C-10 with respect to the carboxylic acid group. Thereafter, the heterologous 12-hydroxylase introduces a hydroxyl group at C-12 with retention of the carbon-carbon unsaturation between C-9 and C-10. In non-limiting examples, the heterologous 12-hydroxylase may be cloned from castor plants such as *Ricinus communis, Lesquerella fendleri, Lesquerella lindheimeri*, or the fungus *Claviceps purpurea*. Glucolipid and sophorolipid formation may then take place in a manner similar to that described above. In this instance, the hydroxycarboxylic acid formed was ricinoleic acid.

Genetically modified yeasts may be capable of introducing a hydroxyl group at C-10, with respect to a carboxylic acid group of the hydroxycarboxylic acid. Specifically, suitable yeasts capable of introducing a hydroxyl group at C-10 may remove the carbon-carbon unsaturation between C-9 and C-10 using a heterologous oleate hydratase to promote hydroxyl group introduction, as explained hereinafter in reference to FIG. 5.

Figure 5:
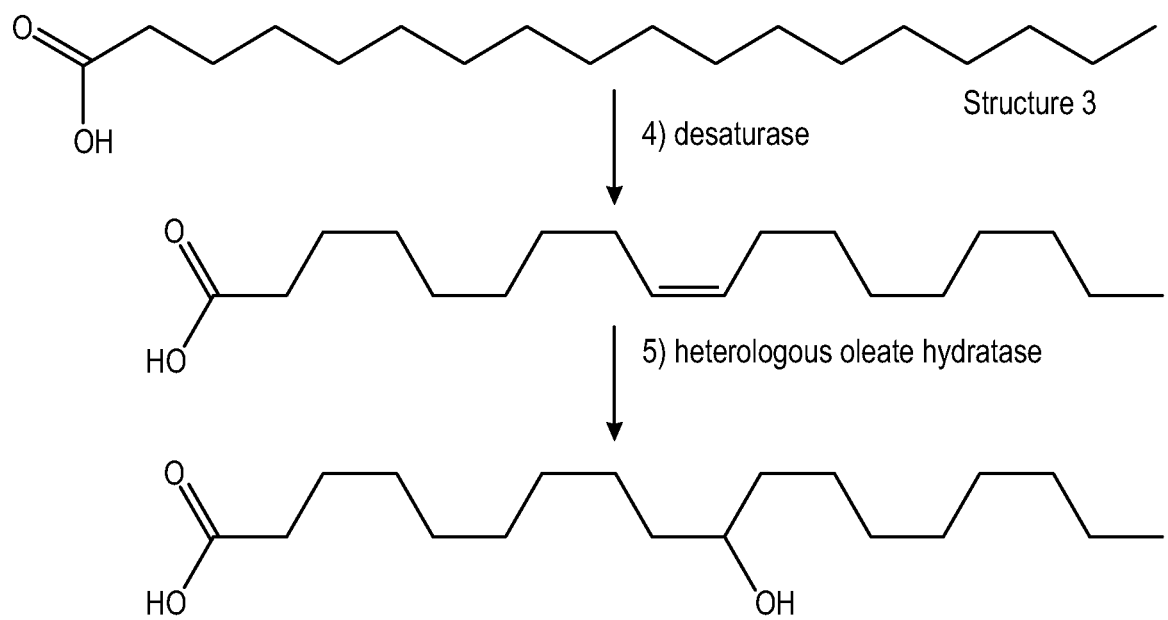
FIG. 5 illustrates a portion of the sequence of enzymatic reactions that an illustrative alkane, octadecane, may undergo to form a C-10 hydroxycarboxylic acid using a genetically modified yeast.

FIG. 5 illustrates a portion of the sequence of enzymatic reactions that an illustrative alkane, octadecane, may undergo to form a C-10 hydroxycarboxylic acid using a genetically modified yeast. The sequence of enzymatic reactions up through the production of stearic acid (Structure 3) is the same as those shown in FIG. 2, and description thereof is not repeated in the interest of brevity. Referring to FIG. 5, desaturase again introduces a double bond between C-9 and C-10 with respect to the carboxylic acid group. Thereafter, the heterologous oleate dehydratase introduces a hydroxyl group at C-10 with concurrent removal of the carbon-carbon unsaturation between C-9 and C-10. In non-limiting examples, heterologous oleate hydratase may be cloned from *Stenotrophomonas nitritireducens, Enterococcus gallinarum, Flavobacterium* sp., *Lactobacillus* sp., *Pediococcus acidilactici*, or *Selenomonas ruminantium*. Glucolipid and sophorolipid formation may then take place in a manner similar to that described above.

In view of the foregoing, still more specific examples of the methods disclosed herein may comprise: providing a normal alkane to a cell culture medium comprising glucose, biosynthesizing a hydroxycarboxylic acid in the cell culture medium by exposing the normal alkane to a microorganism capable of forming the hydroxycarboxylic acid and converting the hydroxycarboxylic acid and glucose into at least one sophorolipid, forming the at least one sophorolipid within the cell culture medium, such that the at least one sophorolipid is secreted from the microorganism and is collected as a lower layer within the cell culture medium, separating the at least one sophorolipid from the cell culture medium, and after separating the at least one sophorolipid from the cell culture medium, hydrolyzing the at least one sophorolipid in an aqueous medium to form the hydroxycarboxylic acid and glucose as free components separate from the cell culture medium. The hydroxycarboxylic acid is present as a phase separate from the aqueous medium and the glucose remains in the aqueous medium. Preferably, the microorganism is a yeast or a genetically modified yeast. Preferably, the hydroxycarboxylic acid may have a carbon chain length of about $C_{14}$-$C_{24}$, more preferably a carbon chain length of $C_{16}$ or $C_{18}$.

As discussed above, the methods of the present disclosure provide glucose in an aqueous medium following hydrolysis and separation of the at least one sophorolipid. The glucose and the aqueous medium can be discarded, if desired, or the glucose obtained as a free component may be recycled to the cell culture medium producing the at least one sophorolipid. Optional blending and/or processing of the aqueous medium to make the aqueous medium suitable for cell growth therein may be conducted, if needed. By recycling the glucose in this manner, the methods of the present disclosure may be made more cost effective and efficient by decreasing the need for supplying external glucose thereto.

The methods of the present disclosure may be conducted with whole cells in the embodiments disclosed above. It is to be appreciated that the concepts and chemical transformations disclosed herein may be performed in a similar manner using one or more isolated enzymes as well. Isolated enzyme methods that may be performed in a manner consistent with the disclosure herein may comprise exposing a hydroxycarboxylic acid to an enzyme cocktail in a first aqueous medium, in which the enzyme cocktail comprises at least glucosyltransferase I, glucosyltransferase II, and lactone esterase and the first aqueous medium comprising glucose. Such methods may further include forming at least one sophorolipid within the first aqueous medium, such that the at least one sophorolipid collects as a lower layer within the first aqueous medium; separating the at least one sophorolipid from the first aqueous medium; and after separating the at least one sophorolipid from the first aqueous medium, hydrolyzing the at least one sophorolipid in a second aqueous medium to form the hydroxycarboxylic acid and glucose as free components separate from the first aqueous medium. As in the corresponding whole cell methods, the hydroxycarboxylic acid is present as a phase separate from the second aqueous medium and the glucose remains in the second aqueous medium. Hydrolysis of the at least one sophorolipid may take place chemically or enzymatically (e.g., using naringinase), as discussed above.

Referring again to the disclosure above, a hydroxycarboxylic acid exposed to glucosyltransferase I, glucosyltransferase II and lactone esterase under suitable conditions may form a lactonic sophorolipid of the hydroxycarboxylic acid. A mixture of acidic sophorolipids and lactonic sophorolipids may be present in some cases. The methods of the present disclosure may further comprise forming the hydroxycarboxylic acid from isolated enzymes as well. More specifically, methods using isolated enzymes may feature an enzyme cocktail further comprising cytochrome P450 monooxygenase, alcohol dehydrogenase, aldehyde dehydrogenase, and desaturase, such that the methods further comprise exposing a carbonaceous feedstock to the enzyme cocktail, and forming the hydroxycarboxylic acid in the first aqueous medium containing the enzyme cocktail. Alternately, a first enzyme cocktail may form the hydroxycarboxylic acid and a second enzyme cocktail may form the at least one sophorolipid from the hydroxycarboxylic acid.

Additional functionality may also be present in a hydroxycarboxylic acid formed using one or more isolated enzymes. In accordance with the disclosure above, the enzyme cocktail may further comprise one or more of 1) methyltransferase and reductase, 2) a heterologous 12-hydroxylase, or 3) a heterologous oleate hydratase. These enzymes may introduce a C-10 methyl branch, a C-12 alcohol hydroxyl group, or a C-10 hydroxyl group depending upon which enzymes are present. If separate enzyme cocktails are used for forming the hydroxycarboxylic acid and the at least one sophorolipid, the foregoing enzymes capable of introducing additional functionality may be present in the first enzyme cocktail.

In light of the disclosure herein, the present disclosure further provides compositions comprising hydroxycarboxylic acids, specifically hydroxycarboxylic acids having a $C_{16}$ or $C_{18}$ backbone, or a reaction product thereof. The term "reaction product" includes any chemical transformation of the hydroxycarboxylic acids, in which the carbon chain length of the hydroxycarboxylic acid is the same as that present before forming the reaction product. Suitable reaction products are discussed below.

Compositions described herein may comprise a functionalized hydroxycarboxylic acid of the present disclosure represented by Structure 4 or a reaction product thereof.

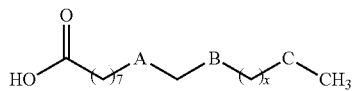

Structure 4

Referring to Structure 4 x is 0, 2, 4, 6, 8 or 10 (preferably 2 or 4), A is cis —CH=CH—, —CH$_2$—CH$_2$—, —CH—CH(CH$_3$)—, or —CH—CH(OH)—, and B and C are —CH$_2$— or —CH(OH)—, provided that the following conditions are met:
1) one of B and C is —CH$_2$— and one of B and C is —CH(OH)—, provided A is not —CH—CH(OH)—, and if A is —CH—CH(OH)—, both B and C are —CH$_2$—; 2) A, B, C and x are chosen such that A, B, C and x are not simultaneously cis —CH=CH—, —CH(OH)—, —CH$_2$—, and 4, respectively; and
3) A, B and C are chosen such that A, B and C are not simultaneously cis —CH=CH—, —CH$_2$—, and —CH(OH)—, respectively.

One particular example of hydroxycarboxylic acids that may be formed according to the present disclosure includes those in which a carbon-carbon unsaturation initially present between C-9 and C-10 is reduced by catalytic hydrogenation to afford the corresponding saturated hydrocarbon. Other conventional chemical reactions of the alkene between C-9 and C-10 may be envisioned by one having ordinary skill in the art (e.g., hydroxylation, epoxidation, and the like, including further reaction thereof) and may be used form functionalized hydroxycarboxylic acids and hydroxycarboxylic acid derivatives that may be suitably present in the compositions disclosed herein.

As such, particular compositions of the present disclosure may include those in which A is —CH$_2$—CH$_2$—, B is —CH$_2$—, and C is —CH(OH)—; or A is —CH$_2$—CH(CH$_3$)—, B is —CH$_2$—, and C is —CH(OH)—; or A is —CH$_2$—CH$_2$— or cis —CH$_2$=CH$_2$—, B is —CH(OH)—, and C is —CH$_2$—; or A is —CH$_2$—CH(OH)—, B is —CH$_2$—, and C is —CH$_2$—. In particular examples of any of the foregoing, n may be 2 or 4 to afford a 16- or 18-carbon backbone for the hydroxycarboxylic acid.

Other reaction products of the functionalized hydroxycarboxylic acids of the present disclosure may include those such as a polyester condensation product of the functionalized hydroxycarboxylic acid, a cyclic diester condensation product of the functionalized hydroxycarboxylic acid, a linear diester condensation product of the functionalized hydroxycarboxylic acid, an ether-linked dimeric dehydration product of the functionalized hydroxycarboxylic acid, a decarboxylated carbon-carbon dimer of the functionalized hydroxycarboxylic acid (ketonic decarboxylation, without or with further reduction), a carboxylic acid derivative of the functionalized hydroxycarboxylic acid, a sophorolipid of the hydroxycarboxylic acid, or any combination thereof. Particular examples of these reaction products for a C-18 hydroxycarboxylic acid are shown consecutively below in Structures 5-10 and Structures 1 and 2. Still other example reaction products may include, for example, a glycerol ester of the hydroxycarboxylic acid, a lactonized form of the hydroxycarboxylic acid, or any combination thereof. Corresponding structures for other functionalized hydroxycarboxylic acids disclosed herein may be envisioned by one having ordinary skill in the art and benefit of the present disclosure.

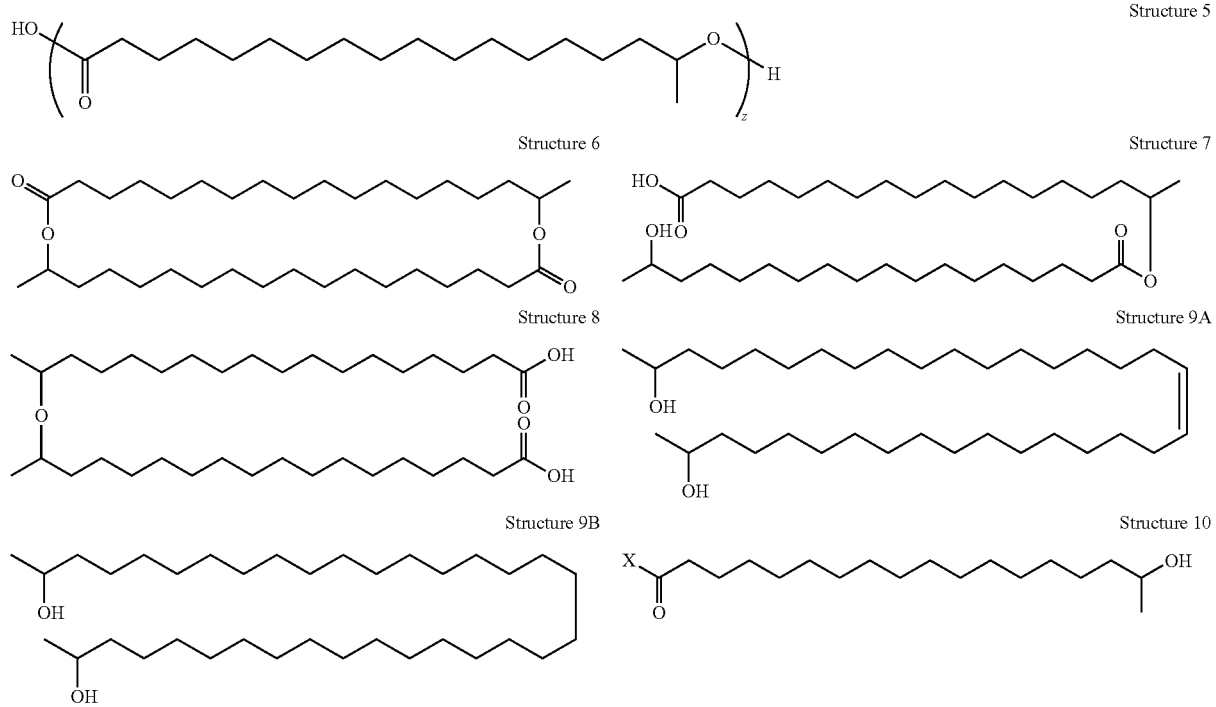

The hydroxycarboxylic acids of the present disclosure may be further blended with various additives to formulate various compositions configured for particular end use applications. Among the additives that may be present to address particular application-specific needs include, for example, base oils, aromatic hydrocarbons, polyalphaolefins, paraffins, esters, ethers, gas-to-liquids base oils, Fischer-Tropsch wax-derived base oils, wax-derived hydroisomerized base oils, silicone oils, antioxidants, corrosion inhibitors, antifoam agents, antiwear agents, dispersants, detergents, viscosity modifiers, and any combination thereof. Suitable examples of additional components that may be present are discussed hereinafter.

A wide range of base oils is known in the art. Base oils that may be useful in the present disclosure include natural oils, mineral oils and synthetic oils, and unconventional oils (or mixtures thereof), any of which can be used unrefined, refined, or rerefined, the latter being also known as reclaimed or reprocessed oil. Unrefined oils include those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve at least one heat transfer fluid base oil property. One skilled in the art will be familiar with many purification processes. Such purification processes may include solvent extraction, secondary distillation, acid extraction, base extraction, filtration, percolation, and any combination thereof. Rerefined oils are obtained by processes analogous to refined oils but using an oil that has been previously used as a feed stock.

Groups I, II, III, IV and V are broad base oil stock categories developed and defined by the American Petroleum Institute (API Publication 1509; www.API.org) to create guidelines for heat transfer fluid base oils. Group I base stocks have a viscosity index of between about 80 to 120 and contain greater than about 0.03% sulfur and/or less than about 90% saturates. Group II base stocks have a viscosity index of between about 80 to 120, and contain less than or equal to about 0.03% sulfur and greater than or equal to about 90% saturates. Group III base stocks have a viscosity index greater than about 120 and contain less than or equal to about 0.03% sulfur and greater than about 90% saturates. Group IV base stocks includes polyalphaolefins (PAOs). Group V base stocks includes base stocks not included in Groups I-IV. Table 1 below summarizes properties of each of these five groups.

TABLE 1

| Base Oil Properties | | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | polyalphaolefins (PAOs) | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale may also be useful. Natural oils also may vary as to the method used for their production and purification, for example, their distillation range and whether they are straight run or cracked, hydrorefined, or solvent extracted.

Group II and/or Group III hydroprocessed or hydrocracked base stocks, including synthetic oils such as alkyl aromatics and synthetic esters are also well known base stock oils that may be used in the disclosure herein.

Synthetic oils include hydrocarbon oil. Hydrocarbon oils include oils such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil base stocks are commonly used synthetic hydrocarbon oil. By way of example, PAOs derived from $C_8$, $C_{10}$, $C_{12}$, or $C_{14}$ olefins or mixtures thereof may be utilized, as described in U.S. Pat. Nos. 4,956,122; 4,827,064; and 4,827,073, each of which is incorporated herein by reference.

Other useful base oil base stocks include wax isomerate base stocks and base oils, comprising hydroisomerized waxy stocks (e.g., waxy stocks such as gas oils, slack waxes, fuels hydrocracker bottoms, and the like), hydroisomerized Fischer-Tropsch waxes, gas-to-liquids (GTL) base stocks and base oils, and other wax isomerate hydroisomerized base stocks and base oils, or mixtures thereof. Fischer-Tropsch waxes, the high boiling point residues of a Fischer-Tropsch synthesis, are highly paraffinic hydrocarbons with very low sulfur content. The hydroprocessing used for the production of such base stocks may use an amorphous hydrocracking/hydroisomerization catalyst, such as one of the specialized lube hydrocracking (LHDC) catalysts or a crystalline hydrocracking/hydroisomerization catalyst, preferably a zeolitic catalyst.

Gas-to-liquids (GTL) base oils, Fischer-Tropsch wax-derived base oils, and other wax-derived hydroisomerized (wax isomerate) base oils may be advantageously used in the present disclosure, and may have useful kinematic viscosities at 100° C. of about 3 cSt to about 50 cSt, preferably about 3 cSt to about 30 cSt, more preferably about 3.5 cSt to about 25 cSt, as exemplified by GTL 4 with kinematic viscosity of about 4.0 cSt at 100° C. and a viscosity index of about 141. These gas-to-liquids (GTL) base oils, Fischer-Tropsch wax-derived base oils, and other wax-derived hydroisomerized base oils may have useful pour points of about −20° C. or lower, and under some conditions may have advantageous pour points of about −25° C. or lower, with useful pour points of about −30° C. to about −40° C. or lower. Useful compositions of gas-to-liquids (GTL) base oils, Fischer-Tropsch wax-derived base oils, and wax-derived hydroisomerized base oils are recited in U.S. Pat. Nos. 6,080,301; 6,090,989; and 6,165,949, for example, and are incorporated herein in their entirety by reference.

Esters may comprise a useful base stock. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, alkyl succinic acid, alkenyl succinic acid, maleic acid, azelaic acid, suberic acid, sebacic acid, fumaric acid, adipic acid, linoleic acid dimer, malonic acid, alkyl malonic acid, alkenyl malonic acid, and the like, with a variety of alcohols such as butyl alcohol, hexyl alcohol, dodecyl alcohol, 2-ethylhexyl alcohol, and the like. Specific examples of these types of esters include dibutyl adipate, di-(2-ethylhexyl) sebacate, di-n-hexyl fumarate, dioctyl sebacate, diisooctyl azelate, diisodecyl azelate, dioctyl phthalate, didecyl phthalate, dieicosyl sebacate, and the like.

Base oils suitable for use in compositions of the present disclosure may include any of the variety of oils corresponding to API Group I, Group II, Group III, Group IV, and Group V oils, and mixtures thereof, preferably API Group II, Group III, Group IV, and Group V oils, and mixtures thereof, more preferably Group III, Group IV, and Group V base oils, and mixtures thereof. Minor quantities of Group I base stock, such as the amount used to dilute additives for blending into formulated lube oil products, can also be used. Even in regard to the Group II stocks, it is preferred that the Group II stock be in the higher quality range associated with that stock, such as a Group II base stock having a viscosity index in the range 100<VI<120.

The base oil may constitute a major component of the compositions of the present disclosure and may be present in an amount ranging from about 50 to about 99 wt. %, preferably from about 70 to about 95 wt. %, and more preferably from about 85 to about 95 wt. %, based on the total weight of the composition. The base oil conveniently has a kinematic viscosity, according to ASTM standards, of about 2.5 cSt to about 12 cSt (or mm$^2$/s) at 100° C. and preferably of about 2.5 cSt to about 9 cSt (or mm$^2$/s) at 100° C. Mixtures of synthetic and natural base oils may be used if desired. Bi-modal mixtures of Group I, II, III, IV, and/or V base stocks may be used, if desired.

Compositions of the present disclosure may additionally contain one or more commonly used heat transfer fluid performance additives including but not limited to antioxidants, corrosion inhibitors, antifoam agents, and others. These additives are commonly delivered with varying amounts of diluent oil, which may range from 5 wt. % to 50 wt. % of the composition. The additives useful in this disclosure do not have to be soluble in the base oil. The types and quantities of performance additives used in the compositions of the present disclosure are not limited by the examples shown herein as illustrations.

The compositions may include at least one antioxidant. Antioxidants retard the oxidative degradation of fluids during service. Such degradation may result in deposits on metal surfaces, the presence of sludge, or a viscosity increase in the heat transfer fluid. One having ordinary skill in the art will appreciate that a wide variety of oxidation inhibitors may be useful in heat transfer fluids. See, Klamann in Lubricants and Related Products, Verlag Chemie, Deerfield Beach, Fla.; ISBN 0-89573-177-0, and U.S. Pat. Nos. 4,798,684 and 5,084,197, for example.

The compositions may include at least one corrosion inhibitor. Corrosion inhibitors are used to reduce the degradation of metallic parts that are in contact with the compositions. Corrosion inhibitors are additives that protect metal surfaces against chemical attack by water or other contaminants. A wide variety of corrosion inhibitors are commercially available. As used herein, corrosion inhibitors include antirust additives and metal deactivators. Suitable corrosion inhibitors also include aryl thiazines, alkyl substituted dimercaptothiodiazoles, alkyl substituted dimercaptothiadiazoles, and mixtures thereof.

One type of suitable corrosion inhibitor is a polar compound that wets the metal surface preferentially, protecting it with a film of oil. Another type of corrosion inhibitor absorbs water by incorporating it in a water-in-oil emulsion so that only the oil touches the metal surface. Yet another type of corrosion inhibitor chemically adheres to the metal to produce a non-reactive surface. Examples of suitable additives include zinc dithiophosphates, metal phenolates, basic metal sulfonates, fatty acids and amines. Such additives may be used in an amount of about 0.01 wt. % to 5 wt. %, preferably about 0.01 to 1.5 wt. %, more preferably 0.01 to 0.2 wt. %, still more preferably 0.01 to 0.1 wt. % (on an as-received basis) based on the total weight of the heat transfer fluid.

Antifoam agents may advantageously be added to the compositions. These agents retard the formation of stable foams. Silicones and organic polymers are typical antifoam agents. For example, polysiloxanes, such as silicon oil or polydimethylsiloxane, provide antifoam properties. Antifoam agents are commercially available and may be used in conventional minor amounts along with other additives such as demulsifiers; usually the amount of these additives combined is less than 1 wt. % and often less than 0.1 wt. %. In an embodiment, such additives may be used in an amount of about 0.01 to 5 wt. %, preferably 0.1 to 3 wt. %, and more preferably about 0.5 to 1.5 wt. %.

The compositions may include at least one antiwear agent. Examples of suitable antiwear agents include oil soluble amine salts of phosphorus compounds, sulphurized olefins, metal dihydrocarbyldithio-phosphates (such as zinc dialkyldithiophosphates), thiocarbamate-containing compounds, such as thiocarbamate esters, thiocarbamate amides, thiocarbamic ethers, alkylene-coupled thiocarbamates, and bis(S-alkyldithiocarbamyl) disulphides.

Antiwear agents used in the compositions may be ashless or ash-forming in nature. Preferably, the antiwear agent is ashless. So-called ashless antiwear agents are materials that form substantially no ash upon combustion. For example, non-metal-containing antiwear agents are considered ashless.

The compositions of the present disclosure may additionally contain one or more other commonly used performance additives including but not limited to dispersants, detergents, viscosity modifiers, metal passivators, ionic liquids, extreme pressure additives, anti-seizure agents, wax modifiers, fluid-loss additives, seal compatibility agents, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0; see also U.S. Pat. No. 7,704,930, the disclosure of which is incorporated herein by reference in its entirety. These additives are commonly delivered with varying amounts of diluent oil, which may range from 5 wt. % to 50 wt. %.

The compositions may include at least one dispersant. During electrical apparatus component operation, oil-insoluble oxidation byproducts are produced. Dispersants help keep these byproducts in solution, thus diminishing their deposition on metal surfaces. Dispersants used in the formulation of the compositions may be ashless or ash-forming in nature. Preferably, the dispersant is ashless. So called ashless dispersants are organic materials that form substantially no ash upon combustion. For example, non-metal-containing or borated metal-free dispersants are considered ashless.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

The compositions may include at least one detergent. Illustrative detergents useful in this disclosure include, for example, alkali metal detergents, alkaline earth metal detergents, or mixtures of one or more alkali metal detergents and one or more alkaline earth metal detergents. A typical detergent is an anionic material that contains a long chain hydrophobic portion of the molecule and a smaller anionic or oleophobic hydrophilic portion of the molecule. The anionic portion of the detergent is typically derived from an organic acid such as a sulfur acid, carboxylic acid (e.g., salicylic acid), phosphorous acid, phenol, or mixtures thereof. The counterion is typically an alkaline earth or alkali metal.

Viscosity modifiers (also known as viscosity index improvers (VI improvers), and viscosity improvers) can be included in the compositions of this disclosure. Viscosity modifiers provide compositions with high and low temperature operability. These additives impart shear stability at elevated temperatures and acceptable viscosity at low temperatures. Suitable viscosity modifiers include high molecular weight hydrocarbons, polyesters and viscosity modifier dispersants that function as both a viscosity modifier and a dispersant. Typical molecular weights of these polymers are about 10,000 to 1,500,000, more typically about 20,000 to 1,200,000, and even more typically between about 50,000 and 1,000,000.

Examples of suitable viscosity modifiers include linear or star-shaped polymers and copolymers of methacrylate, butadiene, olefins, or alkylated styrenes. Polyisobutylene is a commonly used viscosity modifier. Another suitable viscosity modifier is polymethacrylate (copolymers of various chain length alkyl methacrylates, for example), some formulations of which also serve as pour point depressants. Other suitable viscosity modifiers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The compositions may include at least one metal passivator. The metal passivators/deactivators include, for example, benzotriazole, tolyltriazole, 2-mercaptobenzothiazole, dialkyl-2,5-dimercapto-1,3,4-thiadiazole; N,N'-disalicydeneethylenediamine, N,N'-disalicylidenepropylenediamine; zinc dialkyldithiophosphates and dialkyl dithiocarbamates. The metal passivator concentration in the compositions of this disclosure can range from about 0.01 to about 5.0 wt. %, preferably about 0.01 to 3.0 wt. %, and more preferably from about 0.01 wt. % to about 1.5 wt. %, based on the total weight of the heat transfer fluid.

Ionic liquids are so-called salt melts, which are preferably liquid at room temperature and/or by definition have a melting point less than 100° C. They have almost no vapor pressure and therefore have no cavitation properties. In addition, through the choice of the cations and anions in the ionic liquids, the lifetime of the heat transfer fluid may be increased, and by adjusting the electric conductivity, these liquids can be used in equipment in which there is an electric charge buildup, such as electric vehicle components. Suitable cations for ionic liquids include a quaternary ammonium cation, a phosphonium cation, an imidazolium cation, a pyridinium cation, a pyrazolium cation, an oxazolium cation, a pyrrolidinium cation, a piperidinium cation, a thiazolium cation, a guanidinium cation, a morpholinium cation, a trialkylsulfonium cation or a triazolium cation.

In electrical apparatus components, static electricity is generated. To reduce that hazard, a conductive antistatic additive can be added to and distributed throughout the compositions. The compositions will thereby avoid reduction in its performance associated with local breakdown of the base stock and safety problems from static electric build-up.

A class of products called "antistatic fluids" or "antistatic additives," which also are petroleum distillates, can be added to adjust the conductivity of heat transfer fluids to safe levels, such as at or above 100 pico-siemens per meter conductivity. Very small quantities of these antistatic fluids are required to raise the conductivity to the desired levels, such as 10 to 30 milliliters per 1,000 gallons of hydrocarbon.

Conventional pour point depressants (also known as lube oil flow improvers) may be added to the compositions of the present disclosure. Pour point depressants may be added to the compositions of the present disclosure to lower the minimum temperature at which the fluid will flow or can be poured. Examples of suitable pour point depressants include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655, 479; 2,666,746; 2,721,877; 2,721,878; and 3,250,715, each of which is incorporated herein by reference, describe useful pour point depressants and/or the preparation thereof. Such additives may be used in an amount of about 0.01 to 5 wt. %, preferably 0.1 to 3 wt. %, and more preferably about 0.5 to 1.5 wt. %.

The compositions can include at least one seal compatibility agent. Seal compatibility agents help to swell elastomeric seals by causing a chemical reaction in the fluid or physical change in the elastomer. Suitable seal compatibility agents for heat transfer fluids include organic phosphates, aromatic esters, aromatic hydrocarbons, esters (butylbenzyl phthalate, for example), and polybutenyl succinic anhydride. Such additives may be used in an amount of about 0.01 to 5 wt. %, preferably 0.1 to 3 wt. %, and more preferably about 0.5 to 1.5 wt. %.

The compositions can include at least one friction modifier. A friction modifier is any material or materials that can alter the coefficient of friction of a surface. Friction modifiers, also known as friction reducers, or lubricity agents or oiliness agents, and other such agents that change the ability of base oils, formulated heat transfer fluids, or functional fluids, to modify the coefficient of friction of a surface may be effectively used in combination with the base oils or compositions of the present disclosure if desired. Friction modifiers that lower the coefficient of friction are particularly advantageous in combination with the base oils and compositions of this disclosure.

Illustrative friction modifiers may include, for example, organometallic compounds or materials, or mixtures thereof. Illustrative organometallic friction modifiers useful in the heat transfer fluids of this disclosure include, for example, molybdenum amine, molybdenum diamine, an organotungstenate, a molybdenum dithiocarbamate, molybdenum dithiophosphates, molybdenum amine complexes, molybdenum carboxylates, the like, and mixtures thereof. Similar tungsten-based compounds may be preferable.

Other illustrative friction modifiers useful in the compositions of this disclosure include, for example, alkoxylated fatty acid esters, alkanolamides, polyol fatty acid esters, borated glycerol fatty acid esters, fatty alcohol ethers, and mixtures thereof.

The compositions can include at least one extreme pressure agent (EP). EP agents that are soluble in the oil include sulphur- and chlorosulphur-containing EP agents, chlorinated hydrocarbon EP agents and phosphorus EP agents. Examples of such EP agents include chlorinated wax; sulphurised olefins (such as sulphurised isobutylene), organic sulphides and polysulphides such as dibenzyldisulphide, bis-(chlorobenzyl)disulphide, dibutyl tetrasulphide, sulphurised methyl ester of oleic acid, sulphurised alkylphenol, sulphurised dipentene, sulphurised terpene, and sulphurised Diels-Alder adducts; phosphosulphurised hydrocarbons such as the reaction product of phosphorus sulphide with turpentine or methyl oleate; phosphorus esters such as the dihydrocarbon and trihydrocarbon phosphites, including dibutyl phosphite, diheptyl phosphite, dicyclohexyl phosphite, pentylphenyl phosphite; dipentylphenyl phosphite, tridecyl phosphite, distearyl phosphite and polypropylene substituted phenol phosphite; metal thiocarbamates such as zinc dioctyldithiocarbamate and barium heptylphenol diacid; amine salts of alkyl and dialkylphosphoric acids or derivatives; and mixtures thereof (as described in U.S. Pat. No. 3,197,405, which is incorporated herein by reference).

Extreme pressure agents may be used in an amount of about 0.01 to 5 wt. %, preferably 0.01 to 1.5 wt. %, more preferably 0.01 to 0.2 wt. %, and still more preferably 0.01 to 0.1 wt. % (on an as-received basis) based on the total weight of the compositions.

When the compositions contain one or more of the additives discussed above, the additive(s) are blended into the compositions in an amount sufficient for the composition and additive to perform an intended function. Typical amounts of such additives useful in the present disclosure are shown in Table 2 below.

It is noted that many of the additives are shipped from the additive manufacturer as a concentrate, containing one or more additives together, with a certain amount of base oil diluent(s). Accordingly, the weight amounts in the Table 2 below, as well as other amounts mentioned herein, are directed to the amount of active ingredient (that is the non-diluent portion of the ingredient). The wt. % values indicated below are based on the total weight of the composition.

TABLE 2

| Compound | Approximate Wt. % (Useful) | Approximate Wt. % (Preferred) |
| --- | --- | --- |
| Antioxidant | 0.01-5 | 0.1-1.5 |
| Corrosion Inhibitor | 0.01-5 | 0.1-2 |
| Antifoam Agent | 0-3 | 0.001-0.15 |
| Metal Passivator | 0.01-5 | 0.01-1.5 |
| Pour Point Depressant | 0.01-5 | 0.5-1.5 |
| Seal Compatibility Agent | 0.01-5 | 0.5-1.5 |
| Extreme Pressure Agent | 0.01-5 | 0.01-0.1 |

The foregoing additives are all commercially available materials. These additives may be added independently but also may be precombined in packages which can be obtained from suppliers. Additive packages having a variety of ingredients, proportions and characteristics are available and selection of an appropriate package will take the requisite use of the composition into account.

Embodiments Disclosed Herein Include

A. Methods for isolating a hydroxycarboxylic acid using at least one sophorolipid. The methods comprise: obtaining at least one sophorolipid; and hydrolyzing the at least one sophorolipid in an aqueous medium to form glucose and at least one hydroxycarboxylic acid as free components, the at least one hydroxycarboxylic acid being present as phase separate from the aqueous medium and the glucose remaining in the aqueous medium.

B. Methods for producing and isolating a hydroxycarboxylic acid from a carbonaceous feedstock. The methods comprise: biosynthesizing a hydroxycarboxylic acid in a cell culture medium comprising glucose by exposing a carbonaceous feedstock to a microorganism capable of forming at least one sophorolipid; forming at least one sophorolipid from the hydroxycarboxylic acid and glucose within the cell culture medium; separating the at least one sophorolipid from the cell culture medium; and after separating the at least one sophorolipid from the cell culture medium, hydrolyzing the at least one sophorolipid in an aqueous medium to form the hydroxycarboxylic acid and glucose as free components separate from the cell culture medium; wherein the hydroxycarboxylic acid is present as a phase separate from the aqueous medium and the glucose remains in the aqueous medium.

C. Methods for producing and isolating a hydroxycarboxylic acid from a carbonaceous feedstock comprising a normal alkane. The methods comprise: providing a normal alkane to a cell culture medium comprising glucose; biosynthesizing a hydroxycarboxylic acid in the cell culture medium by exposing the normal alkane to a microorganism capable of forming the hydroxycarboxylic acid and converting the hydroxycarboxylic acid and glucose into at least one sophorolipid; forming the at least one sophorolipid within the cell culture medium, at least a portion of the at least one sophorolipid comprising an acidic sophorolipid secreted from the microorganism into the cell culture medium and collecting as a lower layer within the cell culture medium; separating the at least one sophorolipid from the cell culture medium; and after separating the at least one sophorolipid from the cell culture medium, hydrolyzing the at least one sophorolipid in an aqueous medium to form the hydroxycarboxylic acid and glucose as free components separate from the cell culture medium; wherein the hydroxycarboxylic acid is present as a phase separate from the aqueous medium and the glucose remains in the aqueous medium.

D. Methods for forming a hydroxycarboxylic acid from a carbonaceous feedstock using an enzyme cocktail. The methods comprise: exposing a hydroxycarboxylic acid to an enzyme cocktail in a first aqueous medium, the enzyme cocktail comprising at least glucosyltransferase I, glucosyltransferase II, and lactone esterase and the first aqueous medium comprising glucose; forming at least one sophorolipid within the first aqueous medium; wherein the at least one sophorolipid collects as a lower layer within the first aqueous medium; separating the at least one sophorolipid from the first aqueous medium; and after separating the at least one sophorolipid from the first aqueous medium, hydrolyzing the at least one sophorolipid in a second aqueous medium to form the hydroxycarboxylic acid and glucose as free components separate from the first aqueous medium; wherein the hydroxycarboxylic acid is present as a phase separate from the second aqueous medium and the glucose remains in the second aqueous medium.

E. Compositions comprising a functionalized hydroxycarboxylic acid or a reaction product thereof. The compositions comprise: a functionalized hydroxycarboxylic acid represented by Structure 4 or a reaction product thereof.

Structure 4

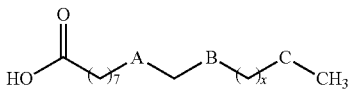

wherein: x is 0, 2, 4, 6, 8 or 10, A is cis —CH=CH—, —CH$_2$—CH$_2$—, —CH—CH(CH$_3$)—, or —CH—CH(OH)—; B and C are independently —CH$_2$— or —CH(OH)—, with provisos that 1) one of B and C is —CH$_2$— and one of B and C is —CH(OH)—, provided A is not —CH—CH(OH)—, and if A is —CH—CH(OH)—, both B and C are —CH$_2$—, 2) A, B, C and x are chosen such that A, B, C and x are not simultaneously cis —CH=CH—, —CH(OH)—, —CH$_2$—, and 4, respectively, and 3) A, B and C are chosen such that A, B and C are not simultaneously cis —CH=CH—, —CH$_2$—, and —CH(OH)—, respectively.

Each of embodiments A-E may have one or more of the following additional elements in any combination:

Element 1: wherein the at least one sophorolipid is hydrolyzed chemically.

Element 2: wherein the at least one sophorolipid is hydrolyzed enzymatically.

Element 3: wherein the method further comprises recycling glucose obtained as a free component to a cell culture medium producing the at least one sophorolipid.

Element 4: wherein the carbonaceous feedstock comprises an alkane, an alkene, a cis olefin, a trans olefin, a geminal substituted olefin, a vicinal substituted olefin, an alpha olefin, a vinylidene olefin, an alkyne, an alkanol, an alkenol, an alkynol, an alkanoic acid, an alkenoic acid, an alkynoic acid, an alkanoic ester, an alkenoic ester, an alkynoic ester, crude oil, a crude oil component, waste oil, vegetable oil, a fat, a lipid, or any combination thereof.

Element 5: wherein the at least one sophorolipid comprises an acidic sophorolipid, a lactonic sophorolipid, or any combination thereof.

Element 6: wherein the microorganism is a yeast.

Element 7: wherein the microorganism is *Starmerella bombicola* (*Candida bombicola*), *Candida albicans*, *Candida floricola*, *Candida apicola*, *Candida riodocensis*, *Candida stellate*, *Candida zemplinina*, *Candida stellata*, *Candida lactis-condensi*, *Candida cellae*, *Candida etchellsii*, *Candida floris*, *Candida sorbosivorans*, *Candida geochares*, *Candida magnoliae*, *Candida vaccinii*, *Candida apis*, *Candida gropengiesseri*, *Candida bombiphila*, *Candida batistae*, *Candida rugosa*, *Candida kuoi*, *Candida tropicalis*, *Cryptococcus* sp., *Torulopsis petrophilum*, *Pichia anomala*, *Rhodotorula bogoriensis*, *Rhodotorula muciliginosa*, *Wickerhamiella domercqiae*, *Cyberlindnera samutprakarnensis*, or any combination thereof.

Element 8: wherein the yeast is genetically modified.

Element 9: wherein the yeast is further capable of introducing carbon-carbon unsaturation within the hydroxycarboxylic acid or a precursor thereof, and the yeast introduces at least one carbon-carbon unsaturation within the hydroxycarboxylic acid or the precursor thereof.

Element 10: wherein the at least one carbon-carbon unsaturation is introduced at C9 and C10 with respect to a carboxylic acid group of the hydroxycarboxylic acid or the precursor thereof.

Element 11: wherein a hydroxyl group of the hydroxycarboxylic acid is located at the ω-1 position.

Element 12: wherein the yeast is further capable of introducing a methyl branch within the hydroxycarboxylic acid or a precursor thereof, and the yeast introduces at least one methyl branch within the hydroxycarboxylic acid or the precursor thereof.

Element 13: wherein the methyl branch is introduced at C10 with respect to a carboxylic acid group of the hydroxycarboxylic acid or the precursor thereof.

Element 14: wherein the yeast is genetically modified to produce methyltransferase and reductase.

Element 15: wherein the yeast is further capable of introducing a hydroxyl group at C12 with respect to a carboxylic acid group of the hydroxycarboxylic acid or a precursor thereof, and the yeast introduces the hydroxyl group at C12 within the hydroxycarboxylic acid or the precursor thereof.

Element 16: wherein the yeast is genetically modified to produce a heterologous 12-hydroxylase.

Element 17: wherein the yeast is further capable of introducing a hydroxyl group at C10 with respect to a carboxylic acid group of the hydroxycarboxylic acid or a precursor thereof, and the yeast introduces the hydroxyl group at C10 within the hydroxycarboxylic acid or the precursor thereof.

Element 18: wherein the yeast is genetically modified to produce a heterologous oleate hydratase.

Element 19: wherein at least a portion of the at least one sophorolipid comprises an acidic sophorolipid secreted from the microorganism into the cell culture medium.

Element 20: wherein at least a portion of the at least one sophorolipid comprises a lactonic sophorolipid formed extracellularly in the cell culture medium.

Element 21: wherein at least a portion of the at least one sophorolipid comprises an acidic sophorolipid obtained by cell lysis of the microorganism.

Element 22: wherein the at least one sophorolipid collects as a lower layer of the cell culture medium.

Element 23: wherein the hydroxycarboxylic acid obtained after hydrolyzing the at least one sophorolipid collects as an upper layer upon the aqueous medium and is separable therefrom.

Element 24: wherein the method further comprises recycling glucose obtained as a free component to the cell culture medium.

Element 25: wherein the enzyme cocktail further comprises naringinase.

Element 26: wherein the enzyme cocktail further comprises cytochrome P450 monooxygenase, alcohol dehydrogenase, aldehyde dehydrogenase, and desaturase, and the method further comprises exposing a carbonaceous feedstock to the enzyme cocktail; and forming the hydroxycarboxylic acid in the first aqueous medium.

Element 27: wherein the hydroxycarboxylic acid has at least one carbon-carbon unsaturation between C9 and C10 with respect to a carboxylic acid group of the hydroxycarboxylic acid and a hydroxyl group at the ω-1 position.

Element 28: wherein the enzyme cocktail further comprises one or more of 1) methyltransferase and reductase, 2) a heterologous 12-hydroxylase, 3) a heterologous oleate hydratase, or any combination thereof.

Element 29: wherein the reaction product comprises one or more of a polyester condensation product of the functionalized hydroxycarboxylic acid, a cyclic diester condensation product of the functionalized hydroxycarboxylic acid, a linear diester condensation product of the functionalized hydroxycarboxylic acid, an ether-linked dimeric dehydration product of the functionalized hydroxycarboxylic acid, a decarboxylated carbon-carbon dimer of the hydroxycarboxylic acid, a carboxylic acid derivative of the hydroxycarboxylic acid, a sophorolipid of the hydroxycarboxylic acid, or any combination thereof.

Element 30: wherein the composition further comprises at least one base stock material.

Element 31: wherein x is 2 or 4.

Element 32: wherein A is —$CH_2$—$CH_2$—, B is —$CH_2$—, and C is —CH(OH)—.

Element 33: wherein A is —$CH_2$—$CH(CH_3)$—, B is —$CH_2$—, and C is —CH(OH)—.

Element 34: wherein A is —$CH_2$—$CH_2$— or cis —$CH_2$=$CH_2$—, B is —CH(OH)—, and C is —$CH_2$—.

Element 35: wherein A is —$CH_2$—CH(OH)—, B is —$CH_2$—, and C is —$CH_2$—.

Element 36: wherein x is 2.

Element 37: wherein x is 4.

By way of non-limiting example, exemplary combinations applicable to A include, but are not limited to, 1 or 2 and 3; 1 or 2 and 5; and 3 and 5. Exemplary combinations applicable to B and C include, but are not limited to, 1 or 2 and 4; 1 or 2 and 5; 1 or 2 and 6; 1 or 2 and 6 and 7; 1 or 2 and 6-8; 1 or 2 and 6-9; 1 or 2 and 6-10; 1 or 2 and 6-11; 1 or 2, 6-9 and 12; 1 or 2, 6-9, 12 and 13; 1 or 2, 6-9 and 14; 1 or 2, 6-9, 14 and 15; 1 or 2, 6-9 and 16; 1 or 2, 6-9, 16 and 17; 1 or 2; 6-9 and 17; 1 or 2, 6-9, 17 and 18; 1 or 2, and 19 or 20; 1 or 2 and 21; 1 or 2 and 2; 1 or 2 and 23; 1 or 2 and 24; 4 and 6; 4 and 6 and 7; 4 and 6-8; 4 and 6-9; 4 and 6-10; 4 and 6-11; 4, 6-9 and 12; 4, 6-9, 12 and 13; 4, 6-9 and 14; 4, 6-9, 14 and 15; 4, 6-9 and 16; 4, 6-9, 16 and 17; 4, 6-9 and 17; 4, 6-9, 17 and 18; 5 and 6; 5 and 6 and 7; 5 and 6-8; 5 and 6-9; 5 and 6-10; 5 and 6-11; 5, 6-9 and 12; 5, 6-9, 12 and 13; 5, 6-9 and 14; 5, 6-9, 14 and 15; 5, 6-9 and 16; 5, 6-9, 16 and 17; 5; 6-9 and 17; 5, 6-9, 17 and 18; 6 and 7; 6-8; 6-9; 6-10; 6-11; 6-9 and 12; 6-9, 12 and 13; 6-9 and 14; 6-9, 14 and 15; 6-9 and 16; 6-9, 16 and 17; 6-9 and 17; 6-9, 17 and 18; 19 or 20 and 6; 19 or 20 and 6 and 7; 19 or 20 and 6-8; 19 or 20 and 6-9; 19 or 20 and 6-10; 19 or 20 and 6-11; 19 or 20, 6-9 and 12; 19 or 20, 6-9, 12 and 13; 19 or 20, 6-9 and 14; 19 or 20, 6-9, 14 and 15; 19 or 20, 6-9 and 16; 19 or 20, 6-9, 16 and 17; 19 or 20, 6-9 and 17; 19 or 20, 6-9, 17 and 18; 21 and 6; 21 and 6 and 7; 21 and 6-8; 21 and 6-9; 21 and 6-10; 21 and 6-11; 21, 6-9 and 12; 21, 6-9, 12 and 13; 21, 6-9 and 14; 21, 6-9, 14 and 15; 21, 6-9 and 16; 21, 6-9, 16 and 17; 21, 6-9 and 17; 21, 6-9, 17 and 18; 22 and 6; 22 and 6 and 7; 22 and 6-8; 22 and 6-9; 22 and 6-10; 22 and 6-11; 22, 6-9 and 12; 22, 6-9, 12 and 13; 22, 6-9 and 14; 22, 6-9, 14 and 15; 22, 6-9 and 16; 22, 6-9, 16 and 17; 22, 6-9 and 17; 22, 6-9, 17 and 18; 23 and 6; 22 and 6 and 7; 23 and 6-8; 23 and 6-9; 23 and 6-10; 23 and 6-11; 23, 6-9 and 12; 23, 6-9, 12 and 13; 23, 6-9 and 14; 23, 6-9, 14 and 15; 23, 6-9 and 16; 23, 6-9, 16 and 17; 23, 6-9 and 17; 23, 6-9, 17 and 18; 24 and 6; 24 and 6 and 7; 24 and 6-8; 24 and 6-9; 24 and 6-10; 24 and 6-11; 24, 6-9 and 12; 24, 6-9, 12 and 13; 24, 6-9 and 14; 24, 6-9, 14 and 15; 24, 6-9 and 16; 24, 6-9, 16 and 17; 24, 6-9 and 17; and 24, 6-9, 17 and 18. Exemplary combinations applicable to D include, but are not limited to 1 and 4; 1 and 5; 1 and 23; 1 and 26; 1 and 27; 1 and 28; 1 and 29; 2 and 4; 4 and 5; 2 and 6; 2 and 23; 2 and 26; 2 and 27; 2 and 28; 2 and 29; 2, 4 and 25; 2, 5 and 25; 2, 25 and 26; 2, 25 and 27; 2, 25 and 28; 2, 25 and 29; 23 and 25; 25 and 26; 25 and 27; 25 and 28; 25 and 29; 26 and 27; 26 and 28; 26 and 29; 27 and 28; 27 and 29; 28 and 29. Exemplary combinations applicable to E include 29 and 30; 31 and 32; 31 and 33; 31 and 34; 31 and 35; 29, 31 and 32; 29, 31 and 33; 29, 31 and 34; 29, 31 and 35; 30-32; 30, 31 and 33; 30, 31 and 34; and 30, 31, and 35.

EMBODIMENTS

Clause 1. A method comprising:
obtaining at least one sophorolipid; and
hydrolyzing the at least one sophorolipid in an aqueous medium to form glucose and at least one hydroxycarboxylic acid as free components, the at least one hydroxycarboxylic acid being present as phase separate from the aqueous medium and the glucose remaining in the aqueous medium.

Clause 2. The method of clause 1, wherein the at least one sophorolipid is hydrolyzed chemically.

Clause 3. The method of clause 1, wherein the at least one sophorolipid is hydrolyzed enzymatically.

Clause 4. The method of any one of clauses 1-3, further comprising:
recycling glucose obtained as a free component to a cell culture medium producing the at least one sophorolipid.

Clause 5. A method comprising:
biosynthesizing a hydroxycarboxylic acid in a cell culture medium comprising glucose by exposing a carbonaceous feedstock to a microorganism capable of forming at least one sophorolipid;
forming at least one sophorolipid from the hydroxycarboxylic acid and glucose within the cell culture medium;
separating the at least one sophorolipid from the cell culture medium; and
after separating the at least one sophorolipid from the cell culture medium, hydrolyzing the at least one sophorolipid in an aqueous medium to form the hydroxycarboxylic acid and glucose as free components separate from the cell culture medium;
wherein the hydroxycarboxylic acid is present as a phase separate from the aqueous medium and the glucose remains in the aqueous medium.

Clause 6. The method of clause 5, wherein the carbonaceous feedstock comprises an alkane, an alkene, a cis olefin, a trans olefin, a geminal substituted olefin, a vicinal substituted olefin, an alpha olefin, a vinylidene olefin, an alkyne, an alkanol, an alkenol, an alkynol, an alkanoic acid, an alkenoic acid, an alkynoic acid, an alkanoic ester, an alkenoic ester, an alkynoic ester, crude oil, a crude oil component, waste oil, vegetable oil, a fat, a lipid, or any combination thereof.

Clause 7. The method of clause 5 or clause 6, wherein the at least one sophorolipid comprises an acidic sophorolipid, a lactonic sophorolipid, or any combination thereof.

Clause 8. The method of any one of clauses 5-7, wherein the microorganism is a yeast.

Clause 9. The method of any one of clauses 5-8, wherein the microorganism is *Starmerella bombicola* (*Candida bombicola*), *Candida albicans*, *Candida floricola*, *Candida apicola*, *Candida riodocensis*, *Candida stellate*, *Candida zemplinina*, *Candida stellata*, *Candida lactis-condensi*, *Candida cellae*, *Candida etchellsii*, *Candida floris*, *Candida sorbosivorans*, *Candida geochares*, *Candida magnoliae*, *Candida vaccinii*, *Candida apis*, *Candida gropengiesseri*, *Candida bombiphila*, *Candida batistae*, *Candida rugosa*, *Candida kuoi*, *Candida tropicalis*, *Cryptococcus* sp., *Torulopsis petrophilum*, *Pichia anomala*, *Rhodotorula bogoriensis*, *Rhodotorula muciliginosa*, *Wickerhamiella domercqiae*, *Cyberlindnera samutprakarnensis*, or any combination thereof.

Clause 10. The method of clause 8 or clause 9, wherein the yeast is genetically modified.

Clause 11. The method of any one of clauses 8-10, wherein the yeast is further capable of introducing carbon-carbon unsaturation within the hydroxycarboxylic acid or a precursor thereof, and the yeast introduces at least one carbon-carbon unsaturation within the hydroxycarboxylic acid or the precursor thereof.

Clause 12. The method of clause 11, wherein the at least one carbon-carbon unsaturation is introduced at C9 and C10 with respect to a carboxylic acid group of the hydroxycarboxylic acid or the precursor thereof.

Clause 13. The method of any one of clauses 8-12, wherein a hydroxyl group of the hydroxycarboxylic acid is located at the ω-1 position.

Clause 14. The method of any one of clauses 8-11, wherein the yeast is further capable of introducing a methyl branch within the hydroxycarboxylic acid or a precursor thereof, and the yeast introduces at least one methyl branch within the hydroxycarboxylic acid or the precursor thereof.

Clause 15. The method of clause 14, wherein the methyl branch is introduced at C10 with respect to a carboxylic acid group of the hydroxycarboxylic acid or the precursor thereof.

Clause 16. The method of clause 15, wherein the yeast is genetically modified to produce methyltransferase and reductase.

Clause 17. The method of any one of clauses 8-11, wherein the yeast is further capable of introducing a hydroxyl group at C12 with respect to a carboxylic acid group of the hydroxycarboxylic acid or a precursor thereof, and the yeast introduces the hydroxyl group at C12 within the hydroxycarboxylic acid or the precursor thereof.

Clause 18. The method of clause 17, wherein the yeast is genetically modified to produce a heterologous 12-hydroxylase.

Clause 19. The method of any one of clauses 8-11, wherein the yeast is further capable of introducing a hydroxyl group at C10 with respect to a carboxylic acid group of the hydroxycarboxylic acid or a precursor thereof, and the yeast introduces the hydroxyl group at C10 within the hydroxycarboxylic acid or the precursor thereof.

Clause 20. The method of clause 19, wherein the yeast is genetically modified to produce a heterologous oleate hydratase.

Clause 21. The method of any one of clauses 5-20, wherein at least a portion of the at least one sophorolipid comprises an acidic sophorolipid secreted from the microorganism into the cell culture medium.

Clause 22. The method of any one of clauses 5-21, wherein at least a portion of the at least one sophorolipid comprises a lactonic sophorolipid formed extracellularly in the cell culture medium.

Clause 23. The method of any one of clauses 5-20, wherein at least a portion of the at least one sophorolipid comprises an acidic sophorolipid obtained by cell lysis of the microorganism.

Clause 24. The method of any one of clauses 21-23, wherein the at least one sophorolipid collects as a lower layer of the cell culture medium.

Clause 25. The method of any one of clauses 5-24, wherein the hydroxycarboxylic acid obtained after hydrolyzing the at least one sophorolipid collects as an upper layer upon the aqueous medium and is separable therefrom.

Clause 26. The method of any one of clauses 5-25, wherein the at least one sophorolipid is hydrolyzed chemically.

Clause 27. The method of any one of clauses 5-25, wherein the at least one sophorolipid is hydrolyzed enzymatically.

Clause 28. The method of any one of clauses 5-27, further comprising:
recycling glucose obtained as a free component to the cell culture medium.

Clause 29. A method comprising:
providing a normal alkane to a cell culture medium comprising glucose;
biosynthesizing a hydroxycarboxylic acid in the cell culture medium by exposing the normal alkane to a microorganism capable of forming the hydroxycarboxylic acid and converting the hydroxycarboxylic acid and glucose into at least one sophorolipid;
forming the at least one sophorolipid within the cell culture medium, at least a portion of the at least one sophorolipid comprising an acidic sophorolipid secreted from the microorganism into the cell culture medium and collecting as a lower layer within the cell culture medium;
separating the at least one sophorolipid from the cell culture medium; and
after separating the at least one sophorolipid from the cell culture medium, hydrolyzing the at least one sophorolipid in an aqueous medium to form the hydroxycarboxylic acid and glucose as free components separate from the cell culture medium;
wherein the hydroxycarboxylic acid is present as a phase separate from the aqueous medium and the glucose remains in the aqueous medium.

Clause 30. The method of clause 29, wherein the at least one sophorolipid comprises an acidic sophorolipid, a lactonic sophorolipid, or any combination thereof.

Clause 31. The method of clause 29 or clause 30, wherein the microorganism is a yeast.

Clause 32. The method of any one of clauses 29-31, wherein the microorganism is *Starmerella bombicola* (*Candida bombicola*), *Candida albicans*, *Candida floricola*, *Candida apicola*, *Candida riodocensis*, *Candida stellate*, *Candida zemplinina*, *Candida stellata*, *Candida lactis-condensi*, *Candida cellae*, *Candida etchellsii*, *Candida floris*, *Candida sorbosivorans*, *Candida geochares*, *Candida magnoliae*, *Candida vaccinii*, *Candida apis*, *Candida gropengiesseri*, *Candida bombiphila*, *Candida batistae*, *Candida rugosa*, *Candida kuoi*, *Candida tropicalis*, *Cryptococcus* sp., *Torulopsis petrophilum*, *Pichia anomala*, *Rhodotorula bogoriensis*, *Rhodotorula muciliginosa*, *Wickerhamiella domercqiae*, *Cyberlindnera samutprakarnensis*, or any combination thereof.

Clause 33. The method of clause 31 or clause 32, wherein the yeast is genetically modified.

Clause 34. The method of any one of clauses 31-33, wherein the yeast is further capable of introducing carbon-carbon unsaturation within the hydroxycarboxylic acid or a precursor thereof, and the yeast introduces at least one carbon-carbon unsaturation within the hydroxycarboxylic acid or the precursor thereof.

Clause 35. The method of clause 34, wherein the at least one carbon-carbon unsaturation is introduced at C9 and C10 with respect to a carboxylic acid group of the hydroxycarboxylic acid or the precursor thereof.

Clause 36. The method of any one of clauses 31-35, wherein a hydroxyl group of the hydroxycarboxylic acid is located at the ω-1 position.

Clause 37. The method of any one of clauses 31-34, wherein the yeast is further capable of introducing a methyl branch within the hydroxycarboxylic acid or a precursor thereof, and the yeast introduces at least one methyl branch within the hydroxycarboxylic acid or the precursor thereof.

Clause 38. The method of clause 37, wherein the methyl branch is introduced at C10 with respect to a carboxylic acid group of the hydroxycarboxylic acid or the precursor thereof.

Clause 39. The method of clause 38, wherein the yeast is genetically modified to produce methyltransferase and reductase.

Clause 40. The method of any one of clauses 31-34, wherein the yeast is further capable of introducing a hydroxyl group at C12 with respect to a carboxylic acid group of the hydroxycarboxylic acid or a precursor thereof, and the yeast introduces the hydroxyl group at C12 within the hydroxycarboxylic acid or the precursor thereof.

Clause 41. The method of clause 40, wherein the yeast is genetically modified to produce a heterologous 12-hydroxylase.

Clause 42. The method of any one of clauses 31-34, wherein the yeast is further capable of introducing a hydroxyl group at C10 with respect to a carboxylic acid group of the hydroxycarboxylic acid or a precursor thereof, and the yeast introduces the hydroxyl group at C10 within the hydroxycarboxylic acid or the precursor thereof.

Clause 43. The method of clause 42, wherein the yeast is genetically modified to produce a heterologous oleate hydratase.

Clause 44. The method of any one of clauses 29-43, wherein at least a portion of the at least one sophorolipid comprises an acidic sophorolipid secreted from the microorganism into the cell culture medium.

Clause 45. The method of any one of clauses 29-44, wherein at least a portion of the at least one sophorolipid comprises a lactonic sophorolipid formed extracellularly in the cell culture medium.

Clause 46. The method of any one of clauses 29-43, wherein at least a portion of the at least one sophorolipid is obtained by cell lysis of the microorganism.

Clause 47. The method of any one of clauses 29-46, wherein the hydroxycarboxylic acid obtained after hydrolyzing the at least one sophorolipid collects as an upper layer upon the aqueous medium and is separable therefrom.

Clause 48. The method of any one of clauses 29-47, wherein the at least one sophorolipid is hydrolyzed chemically.

Clause 49. The method of any one of clauses 29-47, wherein the at least one sophorolipid is hydrolyzed enzymatically.

Clause 50. The method of any one of clauses 29-49, further comprising:
recycling glucose obtained as a free component to the cell culture medium.

Clause 51. A method comprising:
exposing a hydroxycarboxylic acid to an enzyme cocktail in a first aqueous medium, the enzyme cocktail comprising at least glucosyltransferase I, glucosyltransferase II, and lactone esterase and the first aqueous medium comprising glucose;
forming at least one sophorolipid within the first aqueous medium;
wherein the at least one sophorolipid collects as a lower layer within the first aqueous medium;
separating the at least one sophorolipid from the first aqueous medium; and
after separating the at least one sophorolipid from the first aqueous medium, hydrolyzing the at least one sophorolipid in a second aqueous medium to form the hydroxycarboxylic acid and glucose as free components separate from the first aqueous medium;
wherein the hydroxycarboxylic acid is present as a phase separate from the second aqueous medium and the glucose remains in the second aqueous medium.

Clause 52. The method of clause 51, wherein the at least one sophorolipid is hydrolyzed chemically.

Clause 53. The method of clause 51, wherein the at least one sophorolipid is hydrolyzed enzymatically.

Clause 54. The method of clause 51 or clause 53, wherein the enzyme cocktail further comprises naringinase.

Clause 55. The method of any one of clauses 51-54, wherein the enzyme cocktail further comprises cytochrome P450 monooxygenase, alcohol dehydrogenase, aldehyde dehydrogenase, and desaturase, the method further comprising:
exposing a carbonaceous feedstock to the enzyme cocktail; and
forming the hydroxycarboxylic acid in the first aqueous medium.

Clause 56. The method of clause 55, wherein the carbonaceous feedstock comprises an alkane, an alkene, a cis olefin, a trans olefin, a geminal substituted olefin, a vicinal substituted olefin, an alpha olefin, a vinylidene olefin, an alkyne, an alkanol, an alkenol, an alkynol, an alkanoic acid, an alkenoic acid, an alkynoic acid, an alkanoic ester, an alkenoic ester, an alkynoic ester, crude oil, a crude oil component, waste oil, vegetable oil, a fat, a lipid, or any combination thereof.

Clause 57. The method of any one of clauses 51-56, wherein the hydroxycarboxylic acid has at least one carbon-carbon unsaturation between C9 and C10 with respect to a carboxylic acid group of the hydroxycarboxylic acid and a hydroxyl group at the ω-1 position.

Clause 58. The method of any one of clauses 51-56, wherein the enzyme cocktail further comprises one or more of 1) methyltransferase and reductase, 2) a heterologous 12-hydroxylase, 3) a heterologous oleate hydratase, or any combination thereof.

Clause 59. A composition comprising:
a functionalized hydroxycarboxylic acid represented by Structure 4 or a reaction product thereof Structure 4

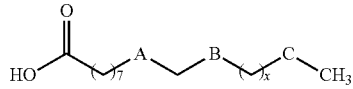

wherein:
x is 0, 2, 4, 6, 8 or 10;
A is cis —CH=CH—, —CH2-CH2-, —CH—CH(CH3)-, or —CH—CH(OH)—;
B and C are independently —CH2- or —CH(OH)—, with provisos that
1) one of B and C is —CH2- and one of B and C is —CH(OH)—, provided A is not —CH—CH(OH)—, and if A is —CH—CH(OH)—, both B and C are —CH2-,
2) A, B, C and x are chosen such that A, B, C and x are not simultaneously cis —CH=CH—, —CH(OH)—, —CH2-, and 4, respectively, and
3) A, B and C are chosen such that A, B and C are not simultaneously cis —CH=CH—, —CH2-, and —CH(OH)—, respectively.

Clause 60. The composition of clause 59, wherein the reaction product comprises one or more of a polyester condensation product of the functionalized hydroxycarboxylic acid, a cyclic diester condensation product of the functionalized hydroxycarboxylic acid, a linear diester condensation product of the functionalized hydroxycarboxylic acid, an ether-linked dimeric dehydration product of the functionalized hydroxycarboxylic acid, a decarboxylated carbon-carbon dimer of the hydroxycarboxylic acid, a carboxylic acid derivative of the hydroxycarboxylic acid, a sophorolipid of the hydroxycarboxylic acid, or any combination thereof.

Clause 61. The composition of clause 59 or clause 60, further comprising:
at least one base stock material.

Clause 62. The composition of any one of clauses 59-61, wherein x is 2 or 4.

Clause 63. The composition of any one of clauses 59-62, wherein A is —CH2-CH2-, B is —CH2-, and C is —CH(OH)—.

Clause 64. The composition of any one of clauses 59-62, wherein A is —CH2-CH($CH_3$)—, B is —CH2-, and C is —CH(OH)—.

Clause 65. The composition of any one of clauses 59-62, wherein A is —CH2-CH2- or cis —CH2=CH2-, B is —CH(OH)—, and C is —CH2-.

Clause 66. The composition of any one of clauses 59-62, wherein A is —CH2-CH(OH)—, B is —CH2-, and C is —CH2-.

Clause 67. The composition of any one of clauses 63-66, wherein x is 2.

Clause 68. The composition of any one of clauses 63, 64 and 66, wherein x is 4.

To facilitate a better understanding of the disclosure herein, the following examples of preferred or representative embodiments are given. In no way should the following examples be read to limit, or to define, the scope of the invention.

EXAMPLES

Cell culturing in the examples was performed in the following manner. To prepare the seed culture, colonies of *Starmerella bombicola* were scraped from a potato-dextrose agar plate and inoculated into 50 mL GYU medium (100 g/L glucose, 10 g/L yeast extract, 1 g/L urea adjusted to pH 5.5-6.0 with HCl, autoclaved at 115° C. for 20 minutes before use) in a 250 mL baffled flask. The seed culture was incubated at 28° C. with rotary shaking at 250 rpm. After 24 hours of cultivation, the $OD_{600\ nm}$ of the culture reached ~13. At this point, 5 mL of the seed culture was inoculated into 50 mL GYU medium containing 10 mL of carbonaceous feedstock.

Example 1: Oxidation of Octadecane to 17-Hydroxyoctadec-9-enoic Acid. Octadecane was introduced to the above glucose-containing cell culture medium containing *S. bombicola* yeast. Kanamycin (50 μg/mL) and ampicillin (100 μg/mL) were added in the culture to prevent bacterial contamination. The culture was incubated at 28° C. for ~30 hours, at which point the cultivation temperature was decreased to 25° C. for a further 7 days of cultivation. The culture was then harvested into a falcon tube and kept refrigerated at 4° C. Octadecane was selectively oxidized intracellularly to stearic acid first by sequential oxidation with cytochrome P450 oxidase, alcohol dehydrogenase and aldehyde dehydrogenase. A double bond was introduced by desaturase at the Δ9 position to afford octadec-9-enoic acid. A hydroxyl group then added at the ω or ω-1 position through selective intracellular oxidation with further cytochrome P450 oxidase oxidation to afford the hydroxycarboxylic acid 17-hydroxy-9-enoic acid (see FIG. 2). Hydroxylation at the ω-1 position occurred preferentially to hydroxylation at the ω position.

Two activated glucose molecules were then coupled consecutively onto the hydroxyl group of the hydroxycarboxylic acid to form the corresponding sophorolipid under mediation of glucosyltransferase I and glucosyltransferase II in the presence of UDP cofactor. The acidic sophorolipid was then secreted into the cell culture medium via sophorolipid transporter protein. Further cyclization of the acidic sophorolipid into the corresponding lactonic sophorolipid may then be promoted by lactoesterase. The lactonic form of the sophorolipid precipitated and was harvested by phase separation from the cell culture medium.

Acid hydrolysis of the harvested sophorolipid was conducted by combining 2 mL of the sophorolipid with 2 mL water. 80 mL of concentrated $H_2SO_4$ (2% v/v) was added and mixed well, and the reaction mixture was heated at 97° C. overnight, with vigorous mixing provided by a stir bar. The mixture was cooled to 55° C., and 2 mL methanol was added to protect the free hydroxycarboxylic acid from self-polymerization. The free hydroxycarboxylic acid was separated as the top layer of a biphasic mixture.

Example 2. Oxidation of 9-Methylenenonadecane. 9-Methylenenonadecane was introduced to the above glucose-containing cell culture medium containing *S. bombicola* yeast. Further culturing was conducted in the same manner as Example 1.

Figure 6:
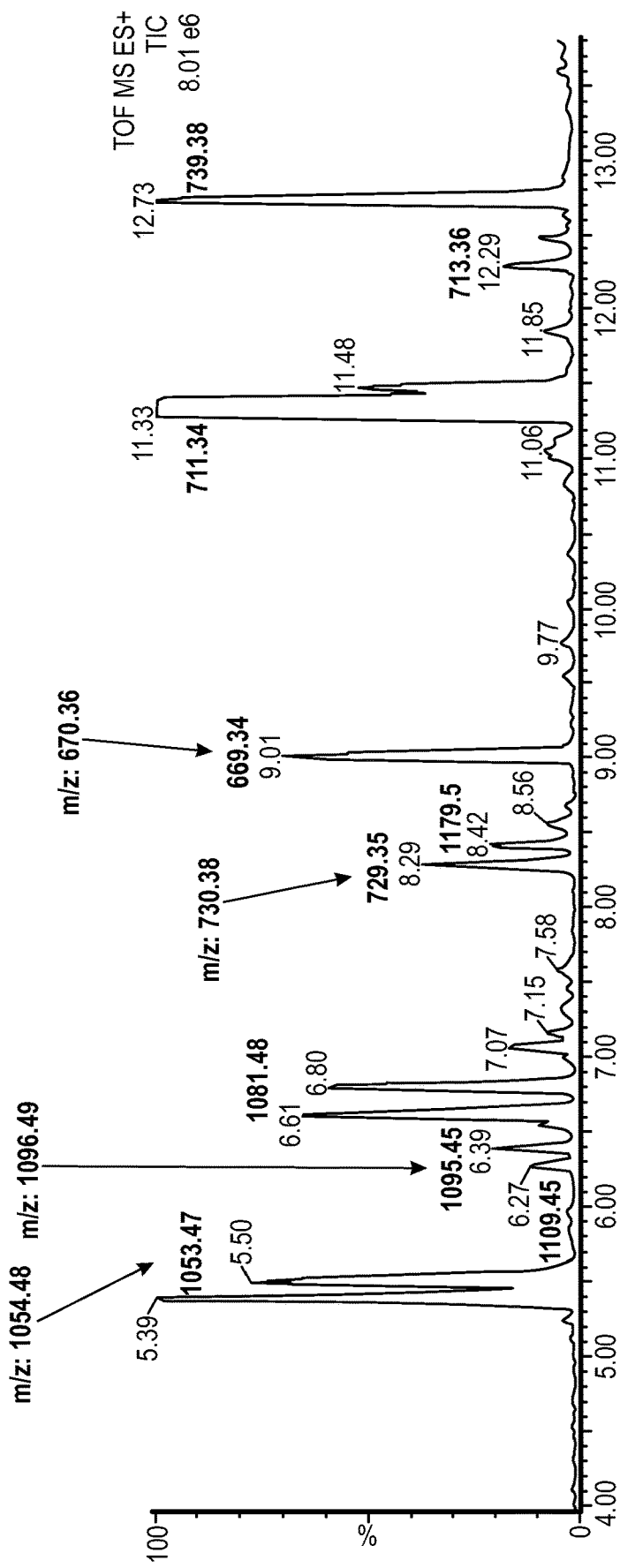
FIG. 6 shows an illustrative LC-MS for the sophorolipids obtained in Example 2.
Figure 7:
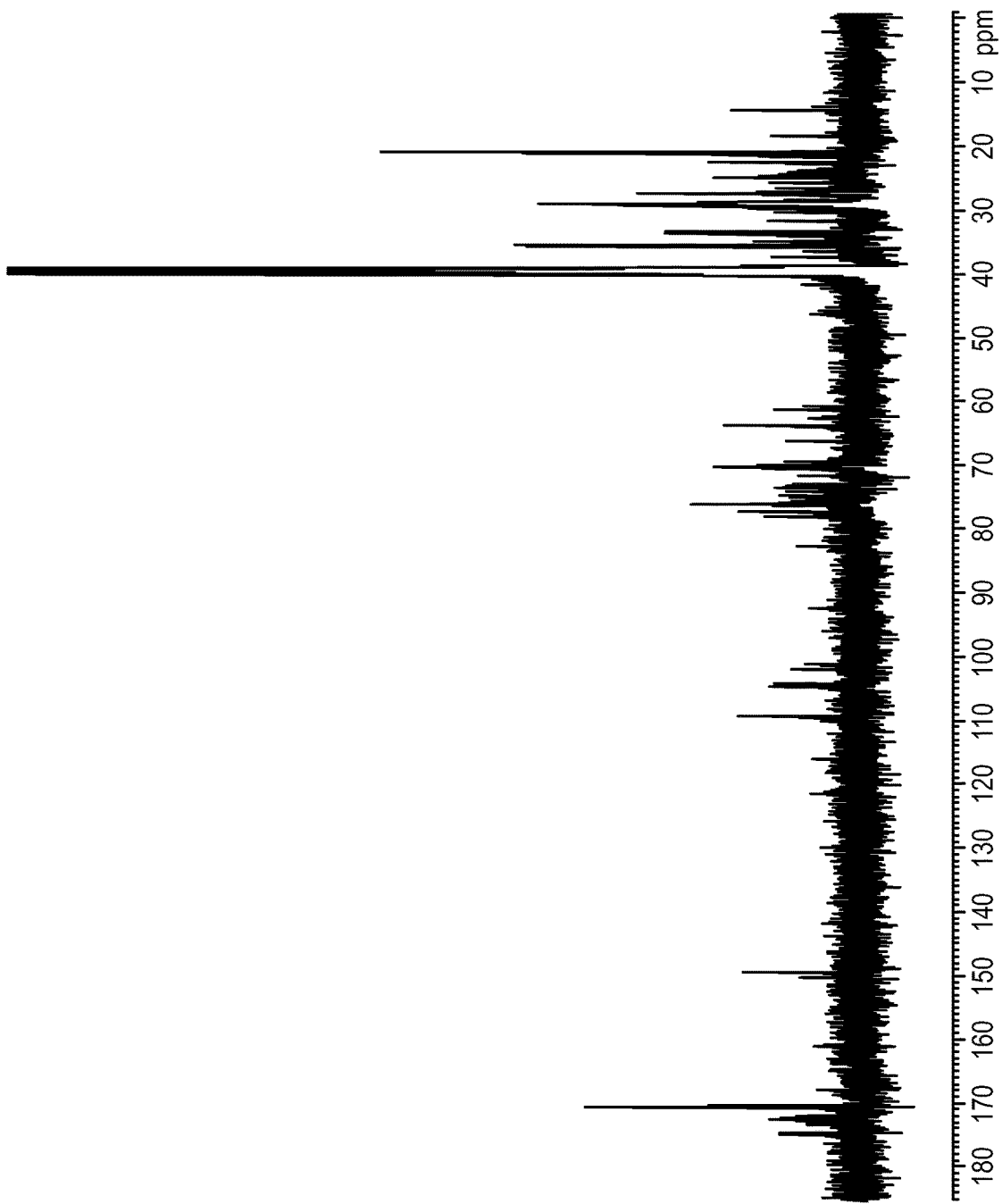
FIG. 7 shows a $^{13}$C NMR spectrum for the sophorolipid product of Example 2.

Upon standing in the refrigerator, a yellow layer of sophorolipids collected at the bottom of the falcon tube. The sophorolipids were collected and analyzed further by LC-MS. FIG. 6 shows an illustrative LC-MS for the sophorolipids obtained in Example 2. FIG. 7 shows a $^{13}$C NMR spectrum for the sophorolipid product of Example 2. The data was consistent with sophorolipid formation.

Figure 8:
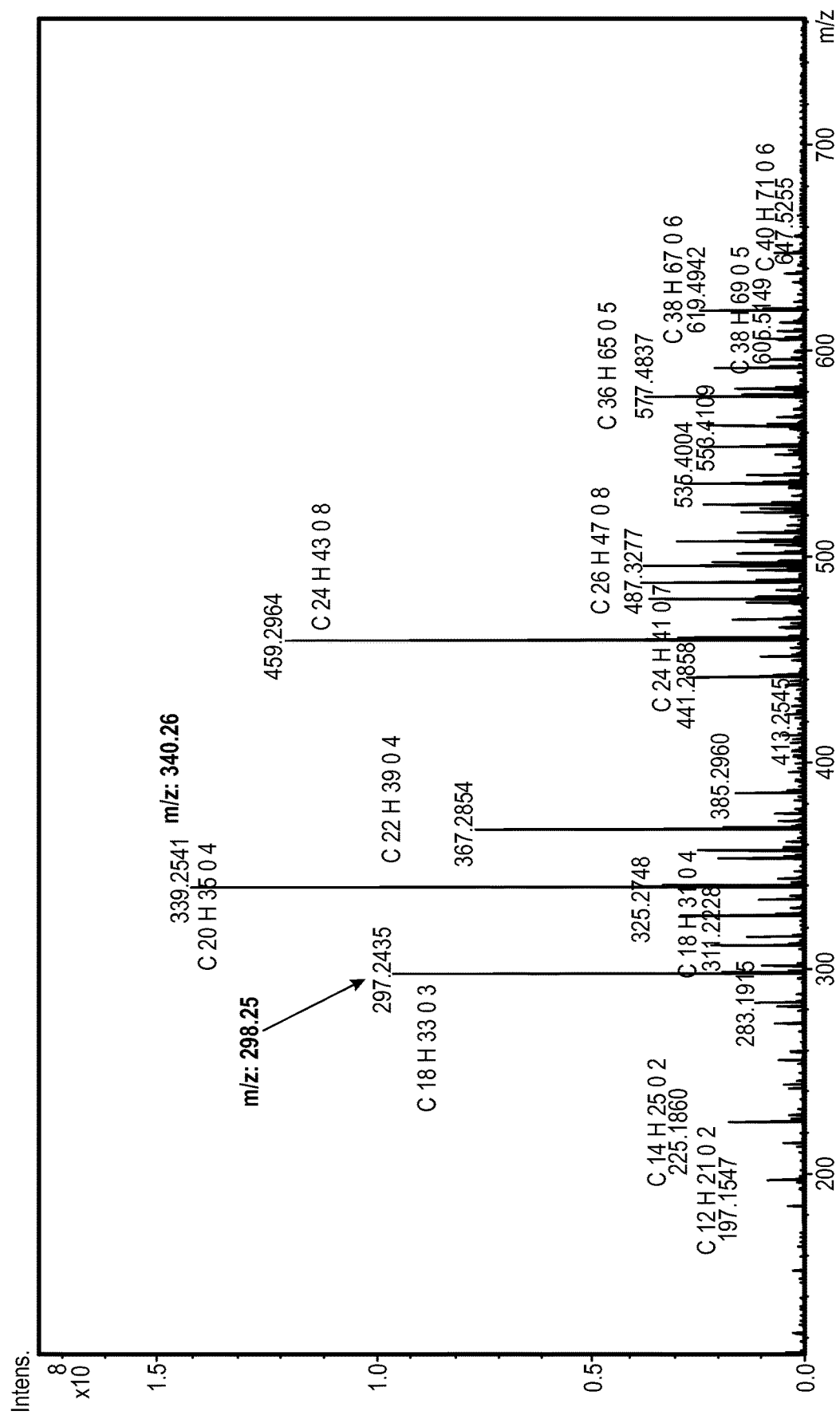
FIG. 8 shows an illustrative FT-ICR spectrum of the hydrolyzed product of Example 2.
Figure 9:
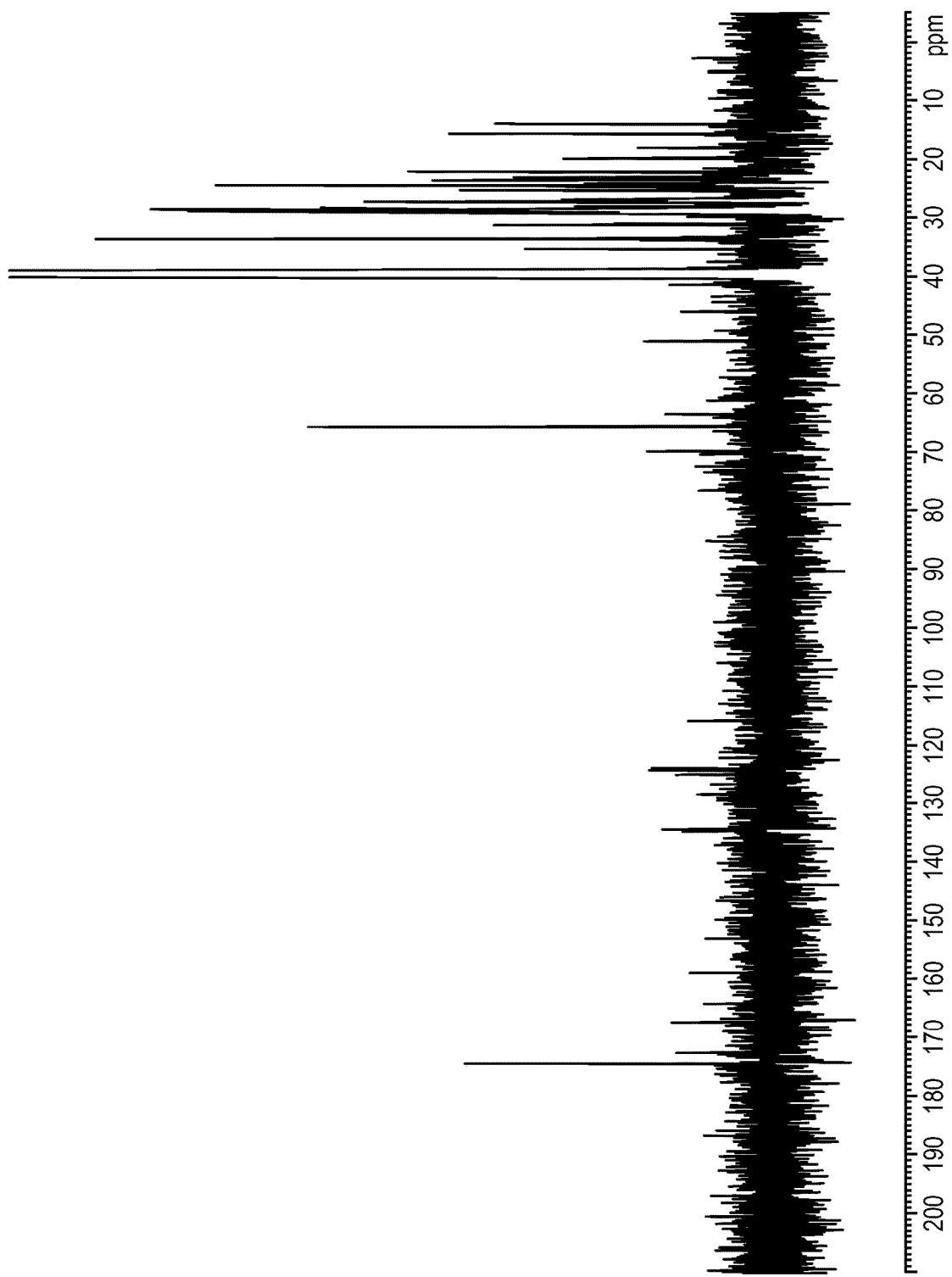
FIG. 9 shows a $^{13}$C NMR spectrum for the hydrolyzed product of Example 2.

Hydrolysis of the sophorolipids was then conducted in the same manner as Example 1. FIG. 8 shows an illustrative FT-ICR mass spectrum of the hydrolyzed product of Example 2. FIG. 9 shows a $^{13}$C NMR spectrum for the hydrolyzed product of Example 2. The data was consistent with sophorolipid hydrolysis and formation of the free hydroxycarboxylic acid.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

The invention claimed is:

1. A method comprising:
biosynthesizing a hydroxycarboxylic acid in a cell culture medium comprising glucose by exposing a carbonaceous feedstock to a microorganism capable of forming at least one sophorolipid;
forming at least one sophorolipid from the hydroxycarboxylic acid and glucose within the cell culture medium;
separating the at least one sophorolipid from the cell culture medium; and after separating the at least one sophorolipid from the cell culture medium, hydrolyzing the at least one sophorolipid in an aqueous medium to form the hydroxycarboxylic acid and glucose as free components separate from the cell culture medium;
wherein the hydroxycarboxylic acid is present as a phase separate from the aqueous medium and the glucose remains in the aqueous medium, and
wherein the microorganism is a yeast and the yeast is genetically modified to produce methyltransferase.

2. The method of claim 1, wherein the carbonaceous feedstock comprises an alkane, an alkene, a cis olefin, a trans olefin, a geminal substituted olefin, a vicinal substituted olefin, an alpha olefin, a vinylidene olefin, an alkyne, an alkanol, an alkenol, an alkynol, an alkanoic acid, an alkenoic acid, an alkynoic acid, an alkanoic ester, an alkenoic ester, an alkynoic ester, crude oil, a crude oil component, waste oil, vegetable oil, a fat, a lipid, or any combination thereof.

3. The method of claim 1, wherein the at least one sophorolipid comprises an acidic sophorolipid, a lactonic sophorolipid, or any combination thereof.

4. The method of claim 1, wherein the microorganism is *Starmerella bombicola* (*Candida bombicola*), *Candida Candida albicans, Candida apicola, Candida riodocensis, Candida stellate, Candida zemplinina, Candida stellata, Candida lactis-conkensi, Candida cellae, Candida etchellsii, Candida floris, Candida sorbosivorans, Candida geochares, Candida magnoliae, Candida vaccinii, Candida apis, Candida gropengiesseri, Candida bombiphila, Candida batistae, Candida rugosa, Candida kuoi, Candida tropicalis, Cryptococcus sp., Torulopsis petrophilum, Pichia anomala, Rhodotorula bogoriensis, Rhodotorula muciliginosa, Wickerhamiella domercqiae, Cyberlindnera samutprakarnensis*, or any combination thereof.

5. The method of claim 1, wherein the yeast is capable of introducing carbon-carbon unsaturation within the hydroxycarboxylic acid or a precursor thereof, and the yeast introduces at least one carbon-carbon unsaturation within the hydroxycarboxylic acid or the precursor thereof.

6. The method of claim 1, wherein a hydroxyl group of the hydroxycarboxylic acid is located at the ω-1 position.

7. The method of claim 4, wherein the yeast is further capable of introducing a methyl branch within the hydroxycarboxylic acid or a precursor thereof, and the yeast introduces at least one methyl branch within the hydroxycarboxylic acid or the precursor thereof.

8. The method of claim 1, wherein the yeast is genetically modified to produce methyltransferase and reductase.

9. The method of claim 1, wherein the yeast is further capable of introducing a hydroxyl group at C12 with respect to a carboxylic acid group of the hydroxycarboxylic acid or a precursor thereof, and the yeast introduces the hydroxyl group at C12 within the hydroxycarboxylic acid or the precursor thereof.

10. The method of claim 1, wherein the yeast is further capable of introducing a hydroxyl group at C10 with respect to a carboxylic acid group of the hydroxycarboxylic acid or a precursor thereof, and the yeast introduces the hydroxyl group at C10 within the hydroxycarboxylic acid or the precursor thereof.

11. The method of claim 1, wherein at least a portion of the at least one sophorolipid comprises an acidic sophorolipid secreted from the microorganism into the cell culture medium.

12. The method of claim 1, wherein at least a portion of the at least one sophorolipid comprises a lactonic sophorolipid formed extracellularly in the cell culture medium.

13. The method of claim 1, wherein at least a portion of the at least one sophorolipid comprises an acidic sophorolipid obtained by cell lysis of the microorganism.

14. The method of claim 1, wherein at least one sophorolipid is hydrolyzed chemically or enzymatically.

15. A method comprising:
  providing a normal alkane to a cell culture medium comprising glucose;
  biosynthesizing a hydroxycarboxylic acid in the cell culture medium by exposing the normal alkane to a microorganism capable of forming the hydroxycarboxylic acid and converting the hydroxycarboxylic acid and glucose into at least one sophorolipid;
  forming the at least one sophorolipid within the cell culture medium, at least a portion of the at least one sophorolipid comprising an acidic sophorolipid secreted from the micrograms into the cell culture medium and collecting as a lower layer within the cell culture medium;
  separating the at least one sophorolipid from the cell culture medium; and
  after separating the at least one sophorolipid from the cell culture medium, hydrolyzing the at least one sophorolipid in an aqueous medium to form the hydroxycarboxylic acid and glucose as free components separate from the cell culture medium;
  wherein the hydroxycarboxylic acid is present as a phase separate from the aqueous medium and the glucose remains in the aqueous medium, and
  wherein the microorganism is a yeast and the yeast is genetically modified to produce methyltransferase.

16. The method of claim 15, wherein the at least one sophorolipid comprises an acidic sophorolipid, a lactonic sophorolipid, or any combination thereof.

17. The method of claim 15, wherein the microorganism is *Starmerella bombicola (Candida bombicola), Candida albicans, Candida floricola, Candida apicola, Candida riodocensis, Candida stellate, Candida zemplinina, Candida stellata, Candida lactis*-condensi, *Candida cellae, Candida etchellsii, Candida floris, Candida sorbosivorans, Candida geochares, Candida magnoliae, Candida vaccinii, Candida apis, Candida gropengiesseri, Candida bombiphila, Candida batistae, Candida rugosa, Candida kuoi, Candida tropicalis, Cryptococcus sp., Torulopsis petrophilum, Pichia anomala, Rhodotorula bogoriensis, Rhodotorula muciliginosa, Wickerhamiella domercqiae, Cyberlindnera samutprakarnensis*, or any combination thereof.

18. The method of claim 15, wherein the yeast is further capable of introducing carbon-carbon unsaturation within the hydroxycarboxylic acid or a precursor thereof, and the yeast introduces at least one carbon-carbon unsaturation within the hydroxycarboxylic acid or the precursor thereof.

19. The method of claim 15 wherein the yeast is further capable of introducing a methyl branch within the hydroxycarboxylic acid or a precursor thereof, and the yeast introduces at least one methyl branch within the hydroxycarboxylic acid or the precursor thereof.

20. The method of claim 15, wherein at least a portion of the at least one sophorolipid comprises an acidic sophorolipid secreted from the micrograms into the cell culture medium.

21. The method of claim 15, wherein at least a portion of the at least one sophorolipid comprises a lactonic sophorolipid formed extracellularly in the cell culture medium.

22. The method of claim 15, wherein at least a portion of the at least one sophorolipid is obtained by cell lysis of the microorganism.

23. The method of claim 15, further comprising:
  recycling glucose obtained as a free component to the cell culture medium.

* * * * *